US012592320B2

(12) United States Patent
Li et al.

(10) Patent No.: US 12,592,320 B2
(45) Date of Patent: Mar. 31, 2026

(54) METHODS OF DETECTING CANCER

(71) Applicants: SeekIn, Inc., Shenzhen, China, Shenzhen (CN); SeekIn Inc., San Diego, CA (US)

(72) Inventors: Shiyong Li, Shenzhen (CN); Wei Wu, Shenzhen (CN); Mao Mao, San Diego, CA (US)

(73) Assignees: SeekIn, Inc., Shenzhen (CN); SeekIn Inc., San Diego, CA (US)

( * ) Notice: Subject to any disclaimer, the term of this patent is extended or adjusted under 35 U.S.C. 154(b) by 0 days.

(21) Appl. No.: 18/620,367

(22) Filed: Mar. 28, 2024

(65) Prior Publication Data

US 2024/0412868 A1      Dec. 12, 2024

(30) Foreign Application Priority Data

Jun. 9, 2023   (WO) ................ PCT/CN2023/099463
Feb. 6, 2024   (WO) ................ PCT/CN2024/076432

(51) Int. Cl.

| | |
|---|---|
| *G16H 50/20* | (2018.01) |
| *G01N 33/575* | (2026.01) |
| *G01N 33/68* | (2006.01) |
| *G06N 20/10* | (2019.01) |
| *G06N 20/20* | (2019.01) |
| *G16H 50/30* | (2018.01) |

(52) U.S. Cl.
CPC ........... *G16H 50/20* (2018.01); *G01N 33/575* (2026.01); *G01N 33/68* (2013.01); *G06N 20/10* (2019.01); *G06N 20/20* (2019.01); *G16H 50/30* (2018.01)

(58) Field of Classification Search
None
See application file for complete search history.

(56) References Cited

U.S. PATENT DOCUMENTS

| | | | |
|---|---|---|---|
| 11,621,080 B2 * | 4/2023 | Cohen et al. | |
| 2013/0288244 A1 | 10/2013 | Deciu et al. | |
| 2017/0024513 A1 | 1/2017 | Lo et al. | |
| 2018/0068083 A1 * | 3/2018 | Cohen et al. | |
| 2018/0307796 A1 | 10/2018 | Jiang et al. | |
| 2020/0005901 A1 * | 1/2020 | Cohen et al. | |
| 2021/0256323 A1 * | 8/2021 | Cohen et al. | |
| 2022/0136062 A1 | 5/2022 | Li et al. | |
| 2023/0223145 A1 * | 7/2023 | Cohen et al. | |
| 2023/0263477 A1 * | 8/2023 | Peichang et al. | |

FOREIGN PATENT DOCUMENTS

| | | |
|---|---|---|
| CN | 101365950 A | 2/2009 |
| CN | 102128876 A | 7/2011 |
| CN | 103484566 A | 1/2014 |
| CN | 106407742 A | 2/2017 |
| CN | 106661614 A | 5/2017 |
| CN | 107292114 A | 10/2017 |
| CN | 107723363 A | 2/2018 |
| CN | 110739027 A | 4/2018 |
| CN | 108322347 A | 7/2018 |
| CN | 108446848 A | 8/2018 |
| CN | 109036571 A | 12/2018 |
| CN | 109097417 A | 12/2018 |
| CN | 111370056 A | 7/2020 |
| CN | 111370057 A | 7/2020 |
| CN | 111370061 A | 7/2020 |
| CN | 112086129 A | 12/2020 |
| CN | 112397143 A | 2/2021 |
| CN | 112410422 A | 2/2021 |
| CN | 112927755 A | 6/2021 |
| CN | 117831690 A | 4/2024 |
| WO | WO 2016/090584 A1 | 6/2016 |
| WO | WO 2016094330 A2 | 6/2016 |
| WO | WO 2016/135478 A1 | 9/2018 |
| WO | WO 2019/018374 A1 | 1/2019 |
| WO | WO 2019/047181 A1 | 3/2019 |
| WO | WO 2020/094775 A1 | 5/2020 |
| WO | WO 2024/250730 A1 | 12/2024 |

OTHER PUBLICATIONS

Holdenrieder, Stefan et al. "Clinically Meaningful Use of Blood Tumor Markers in Oncology." BioMed Research International 2016 (2016): 1-10. Web. (Year: 2016).*

Mizono et al. "Clinical Utility of Tumor Markers." Open Journal of Pathology n. pag. Web. (Year: 2021).*

Fortner, Renée T et al. "Correlates of Circulating Ovarian Cancer Early Detection Markers and Their Contribution to Discrimination of Early Detection Models: Results from the EPIC Cohort." Journal of ovarian research 10.1 (2017): 20-. Web. (Year: 2017).*

Molina, Rafael et al. "Assessment of a Combined Panel of Six Serum Tumor Markers for Lung Cancer." American journal of respiratory and critical care medicine 193.4 (2016): 427-437. Web. (Year: 2016).*

Addeo et al., "Measuring tumor mutation burden in cell-free DNA: advantages and limits," Translational Lung Cancer Research, Aug. 2019, 8(4):553-555.

Babayan et al., "Advances in liquid biopsy approaches for early detection and monitoring of cancer," Genome Medicine, Mar. 20, 2018, 10:21, 3 pages.

Chang et al., "Non-invasive detection of lymphoma with circulating tumor DNA features and protein tumor markers," Frontiers, Jan. 19, 2024, 13 pages.

Cohen et al., "Detection and localization of surgically resectable cancers with a multi-analyte blood test," Science, Feb. 23, 2018, 359(6378):926-930.

(Continued)

*Primary Examiner* — Anna Skibinsky

*Assistant Examiner* — Joseph Pulliam

(74) *Attorney, Agent, or Firm* — Fish & Richardson P.C.

(57) ABSTRACT

The disclosure is related to methods of cancer early detection. In some embodiments, a panel of selected protein tumor markers are used for effective and affordable multi-cancer early detection.

17 Claims, 6 Drawing Sheets

(56) References Cited

OTHER PUBLICATIONS

Del Villano et al., "Radioimmunometric assay for a monoclonal antibody-defined tumor marker, CA 19-9," Clinical Chemistry, Mar. 1, 1983, 29(3):549-552 (Abstract Only).

Gusnanto et al., "Estimating optimal window size for analysis of low-coverage next-generation sequence data," Bioinformatics, Jul. 1, 2014, 30(13):1823-1829.

Ji et al., "Identifying occult maternal malignancies from 1/93 million pregnant women undergoing noninvasive prenatal screening tests," Genetics in Medicine, Apr. 12, 2019, 10 pages.

Li et al., "HIVID: An efficient method to detect HBV integration using low coverage sequencing," Genomics, Oct. 2013, 102(4):338-344.

Li et al., "Mapping short DNA sequencing reads and calling variants using mapping quality score," Genome Res., Aug. 19, 2008, 18:1851-1858.

Locker et al., "ASCO 2006 Update of Recommendations for the Use of Tumor Markers in Gastrointestinal Cancer," Journal of Clinical Oncology, Nov. 20, 2006, 24(33):5313-5327.

Muraro et al., "Generation and Characterization of B72.3 Second Generation Monoclonal Antibodies Reactive with the Tumor-Associated Glycoprotein 72 Antigen," Cancer Research, Aug. 15, 1988, 48(16):4588-4596.

Rizvi et al., "Mutational landscape determines sensitivity to PD-1 blockade in non-small cell lung cancer," Science, Apr. 3, 2015, 348(6230):124-128.

Ulrich et al., "Cell-free DNA in oncology: gearing up for clinic," Annals of Laboratory Medicine, 2018, 38(1):1-8.

Zhu, et al., "Circulating cell-free DNA fragmentation is a stepwise and conserved process linked to apoptosis," BMC Biology, Nov. 13, 2023, 21(1):1-11.

Shendure et al., "DNA sequencing at 40: past, present and future," Nature, Oct. 19, 2017, 550:345-353.

Extended European Search Report in European Appln. No. 24709628.2, mailed on Sep. 5, 2025, 16 pages.

Fang et al., "Practical stability assessment of whole-genome methylation sequencing of plasma cell-free DNA," Chinese Journal of Biotechnology, Dec. 25, 2019, 35(12):2284-2294 (with English Abstract).

Iglewicz et al., "Outlier Labeling," How to Detect and Handle Outliers, Nov. 8, 1993, Chapter 3, pp. 9-17.

Jiang et al., "Lengthening and shortening of plasma DNA in hepatocellular carcinoma patients," Proceedings of the National Academy of Sciences of the United States of America, Feb. 2, 2015, 112(11):E1317-E1325.

Luan et al., "A panel of seven protein tumour markers for effective and affordable multi-cancer early detection by artificial intelligence: a large-scale and multicentre case-control study," Eclinical Medicine, Jul. 15, 2023, 51(1):102041, 12 pages.

Shi et al., "Rare Germline Copy Number Variations and Disease Susceptibility in Familial Melanoma," Journal of Investigative Dermatology, Dec. 31, 2016, 136(12):2436-2443.

Tu et al., "A panel of seven protein tumor markers for multi-cancer early detection by artificial intelligence, " Journal of Clinical Oncology, May 31, 2023, 41(1):3067.

Wang et al., "Advances in the study of predictive markers of immunotherapy for non-small cell lung cancer based on PD-1/PD-L1 inhibitors," Modern Oncology, May 31, 2021, 29(10):1822-1825 (with English Abstract).

Zhu et al., "Recent Ex Vivo Gene Therapy through Genome Editing, " Chinese Journal of Cell Biology, Apr. 2019, 41(4):573-582 (with English Abstract).

* cited by examiner

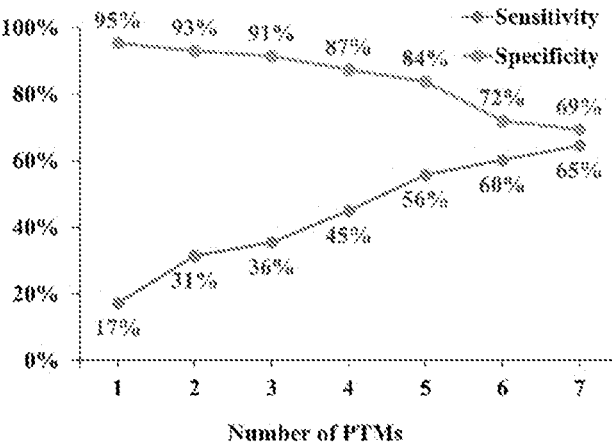

FIG. 4

| | Conventional clinical method | | AI method | |
|---|---|---|---|---|
| | Cancer | Non-cancer | Cancer | Non-cancer |
| Predict cancer | 1249* | 3200* | 1012 | 527 |
| Predict non-cancer | 710 | 4223 | 947 | 6896 |
| Sensitivity (95% CI) | 63·8% (61·6%, 65·9%) | | 51·7% (49·4%, 53·9%) | |
| Specificity (95% CI) | 56·9% (55·8%, 58·0%) | | 92·9% (92·3%, 93·5%) | |
| PPV (95% CI) | 28·1% (26·8%, 29·4%) | | 65·8% (63·3%, 68·1%) | |
| NPV (95% CI) | 85·6% (84·6%, 86·6%) | | 87·9% (87·2%, 88·6%) | |

*Individuals with at least one of the markers included in the panel showing values above the cut-off point were considered as being positive. PPV, positive predictive value. NPV, negative predictive value.

FIG. 5

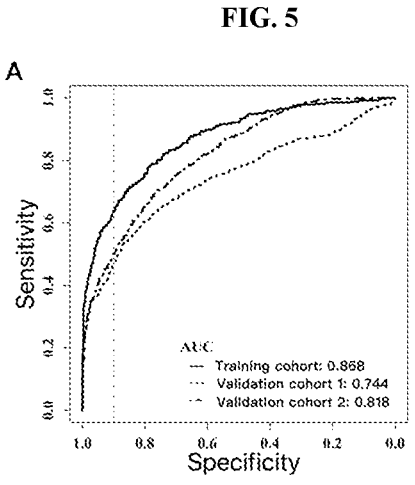

FIG. 6A

METHODS OF DETECTING CANCER

CROSS REFERENCE TO RELATED APPLICATIONS

This application claims priority to International Application No. PCT/CN2024/076432, filed with the State Intellectual Property Office of the People's Republic of China on Feb. 6, 2024, and claims priority to International Application No. PCT/CN2023/099463, filed with the State Intellectual Property Office of the People's Republic of China on Jun. 9, 2023, the contents of which are hereby incorporated by reference in their entireties.

TECHNICAL FIELD

The present disclosure relates to methods for multi-cancer early detection based on selected protein tumor markers. The disclosure is also related to prediction of affected tissue of origin for those who have been detected with cancer.

BACKGROUND

Multi-cancer early detection aims at reducing cancer deaths. Unfortunately, many established cancer screening technologies are not suitable for use in low- and middle-income countries (LMICs) due to cost, complexity; and dependency on extensive medical infrastructure. Thus, many patients with cancer can be cured if diagnosed early and treated effectively. At present the majority of deadly cancers do not have standard-of-care screening methods available. Therefore, a non-invasive and efficient multi-cancer early detection (MCED) test is a highly unmet need. And most importantly, the test should be simple and affordable, which is also suitable for LMICs.

SUMMARY

The present disclosure provided a blood-based multi-cancer early detection (MCED) test. The MCED test is used to find more than one type of cancer from a single sample of blood. In some embodiments, this method integrates the measurement of a panel of seven or ten selected protein tumor markers (PTMs) and clinical information of the individual for MCED and predicting affected tissue of origin (TOO), empowered by artificial intelligence (AI) technology. As shown in the present disclosure, in one large study (n=9382) containing more than nine common cancer types and dominated by early-stage patients (63.2% stage I and II), the performance of the methods as described herein was significantly superior to the conventional clinical method that has a specifity such as 56.9%. The test achieved a sensitivity of 51.7% with a specificity of 92.9%, resulting in 84.3% accuracy, with 49.5% sensitivity in stage I and II patients. In addition, the overall accuracy of TOO prediction in the true positives was 66.8%.

The methods as descried herein can be used alongside with some other existing screening approaches, and can offer the potential to find more types of cancer at earlier stages using one tube of blood, to improve patient outcomes by treating the disease when it is typically most responsive to therapy, and ultimately to have a profound impact on public health.

In one aspect, the disclosure is related to a computer implemented method for early detection of the presence of cancer in a subject, the method comprising: (a) quantifying the level of a panel of biomarkers from the blood sample of the subject, wherein the panel of biomarkers comprises at least 1, 2, 3, 4, 5, 6, 7, 8, 9 or 10 biomarkers selected from alpha-fetoprotein (AFP), carbohydrate antigen 125 (also known as cancer antigen 125, or CA125), carbohydrate antigen 15-3 (also known as cancer antigen 15-3, or CA15-3), carbohydrate antigen 19-9 (also known as cancer antigen 19-9, CA19-9, sialyl Lewis (a) or sialylated Lewis (a) antigen), carbohydrate antigen 72-4 (also known as cancer antigen 72-4, CA 72-4, or tumor-associated glycoprotein (TAG) 72), carcinoembryonic antigen (CEA), cytokeratin 19 fragments (also known as CYFRA 21-1), pro-gastrin-releasing peptide (ProGRP), squamous cell carcinoma antigen (also known as SCC, SCCA, including SCCA1 and SCCA2), and total prostate-specific antigen (also known as PSA, TPSA, or KLK3): (b) selecting a plurality of parameters for inputs into a machine learning system, wherein the plurality of parameters comprises the level of the panel of biomarkers: (c) training the machine learning system using a machine learning algorithm selected from the group consisting of Generalized Linear Model (GLM), Gradient Boosting Machine (GBM), Random Forest (RF), and Support Vector Machine (SVM); and (d) determining a cancer predicting score. In some embodiments, a high cancer predicting score indicates a high probability of the subject to have cancer. In some embodiments, the plurality of parameters further comprises at least one clinical parameter (e.g., age, gender, and/or smoking status). In some embodiments, the plurality of parameters further comprises X-ray imaging, mammography, computerized tomography (CT), and/or Magnetic Resonance Imaging (MRI).

In some embodiments, the panel of biomarkers are selected from at least seven different biomarkers selected from AFP, CA125, CA15-3, CA19-9, CA72-4, CEA, CYFRA 21-1, ProGRP, SCC, and PSA.

In some embodiments, the panel of biomarkers are selected from at least 1, 2, 3, 4, 5, 6, 7, 8, or 9 different biomarkers selected from AFP, CA125, CA15-3, CA19-9, CEA, CYFRA 21-1, ProGRP, SCC, and PSA.

In some embodiments, the panel of biomarkers are selected from at least seven different biomarkers selected from AFP, CA125, CA15-3, CA19-9, CEA, CYFRA 21-1, ProGRP, SCC, and PSA.

In some embodiments, the panel of biomarkers comprises AFP, CA125, CA15-3, CA19-9, CA72-4, CEA, and CYFRA 21-1. In some embodiments, the panel of biomarkers consists of AFP, CA125, CA15-3, CA19-9, CA72-4, CEA, and CYFRA 21-1. In some embodiments, the panel of biomarkers comprises AFP, CA125, CA15-3, CA19-9, CA72-4, CEA, CYFRA 21-1, ProGRP, SCC, and PSA. In some embodiments, the panel of biomarkers consists of AFP, CA125, CA15-3, CA19-9, CA72-4, CEA, CYFRA 21-1, ProGRP, SCC, and PSA.

In some embodiments, the panel of biomarkers comprises or consists of CEA, CYFRA 21-1, SCC, and ProGRP.

In some embodiments, the subject is a male, and the panel of biomarkers comprises or consists of AFP, CA125, CA15-3, CA19-9, CEA, CYFRA 21-1, ProGRP, SCC, and PSA.

In some embodiments, the subject is a female, and the panel of biomarkers comprises or consists of AFP. CA125, CA15-3, CA19-9, CEA, CYFRA 21-1, ProGRP, and SCC.

In some embodiments, the machine learning system is trained using GLM. In some embodiments, the method comprises training the machine learning system using at least two machine learning algorithms selected from the group of GLM, GBM, RF, and SVM. In some embodiments, the method comprises applying GLM to the results from the at least two machine learning algorithms. In some embodiments, the quantified level of the panel of biomarkers is normalized by Modified Z-Score. In some embodiments, the Modified Z-Score is obtained by calculating the difference between the observed value and the median value, divided by the median absolute deviation (MAD). In some embodiments, the method can aid early detection of the presence of at least two cancer types simultaneously. In some embodiments, the cancer is pancreatic cancer, ovarian cancer, liver cancer (e.g., hepatocellular carcinoma), lung cancer, stomach cancer, colorectal cancer, lymphoma, oesophageal cancer, prostate cancer, or breast cancer. In some embodiments, the cancer is a stage I cancer, a stage II cancer, a stage III cancer, or a stage IV cancer. In some embodiments, the method further comprises an Outlier Analysis. In some embodiments, a value of a biomarker that is higher than a cut-off value indicates that the subject has a cancer.

In one aspect, the disclosure is related to a computer implemented method for identifying tissue of origin (TOO) in a cancer subject, the method comprising: (a) quantifying the level of a panel of biomarkers from the blood sample of the subject, in some embodiments, the panel of biomarkers are selected from at least 1, 2, 3, 4, 5, 6, 7, 8, 9, or 10 biomarkers selected from AFP, CA125, CA15-3, CA19-9, CA72-4, CEA, CYFRA 21-1. ProGRP, SCC, and PSA; (b) selecting a plurality of parameters for inputs into a machine learning system, in some embodiments, the plurality of parameters comprises the level of the panel of biomarkers; (c) training the machine learning system using Random Forest (RF) or Gradient Boosting Machine (GBM); and (d) determining the TOO based on the machine learning system. In some embodiments, the plurality of parameters further comprises at least one clinical parameter selected from age and gender.

In some embodiments, the panel of biomarkers are selected from at least 7 biomarkers selected from AFP. CA125, CA15-3, CA19-9, CA72-4, CEA, CYFRA 21-1, ProGRP. SCC, and PSA.

In some embodiments, the panel of biomarkers are selected from at least 1, 2, 3, 4, 5, 6, 7, 8, or 9 different biomarkers selected from AFP, CA125, CA15-3, CA19-9, CEA, CYFRA 21-1, ProGRP. SCC, and PSA. In some embodiments, the panel of biomarkers are selected from at least 7 different biomarkers selected from AFP, CA125, CA15-3, CA19-9, CEA, CYFRA 21-1, ProGRP. SCC, and PSA.

In some embodiments, the subject is a male, and the panel of biomarkers comprises or consists of AFP, CA125, CA15-3, CA19-9, CEA, CYFRA 21-1, ProGRP, SCC, and PSA.

In some embodiments, the subject is a female, and the panel of biomarkers comprises or consists of AFP. CA125, CA15-3, CA19-9, CEA, CYFRA 21-1, ProGRP, and SCC.

In some embodiments, the panel of biomarkers comprises or consists of AFP, CA125, CA15-3, CA19-9, CA72-4, CEA, and CYFRA 21-1. In some embodiments, the panel of biomarkers comprises or consists of AFP. CA125, CA15-3, CA19-9, CA72-4, CEA, CYFRA 21-1, ProGRP. SCC, and PSA.

In some embodiments, the panel of biomarkers comprises or consists of CEA, CYFRA 21-1, SCC, and ProGRP.

In some embodiments, the cancer is pancreatic cancer, ovarian cancer, liver cancer (e.g., hepatocellular carcinoma), lung cancer, stomach cancer, colorectal cancer, lymphoma, oesophageal cancer, prostate cancer, small cell lung cancer (SCLC), cervical cancer, or breast cancer.

In one aspect, the disclosure is related to a computer implemented method of training a machine learning system to generate a classifier for use to identify a subject likely to have cancer, the method comprising: (a) storing a set of data comprising a plurality of subject records from more than 1000 subjects, each subject record including a plurality of parameters and corresponding values for each subject included in the subject records, and a diagnostic indicator indicating whether or not the subject included in the subject records has been diagnosed with a cancer; (b) selecting a subset of the plurality of parameters for inputs into the machine learning system, in some embodiments, the subset consists of a panel of the biomarkers selected from at least 1, 2, 3, 4, 5, 6, 7, 8, 9, or 10 different biomarkers selected from AFP. CA125, CA15-3, CA19-9, CA72-4, CEA, CYFRA 21-1, ProGRP. SCC, and PSA; (c) randomly partitioning the set of data into training data and validation data; and (d) generating the classifier. In some embodiments, the method further comprises determining the outlier cut-off value for each biomarker. The cut-off value can be determined by, e.g., Box plot method, Percentile method, Modified Z-score. A subject with a biomarker with a value higher than outlier cut-off value is predicted as cancer.

In some embodiments, the machine learning system is trained based on the training data and the subset of inputs. In some embodiments, the classifier is trained with a sensitivity of at least 50% and a specificity of at least 90%, for correct classification of the subject as likely to have cancer or not, whereby the machine learning system is trained to generate the classifier. In some embodiments, the classifier, when used with individual subject data, generates a composite algorithm value that is converted to a probability of cancer (POC) relative to a cohort population.

In some embodiments, the panel of biomarkers are selected from at least 7 biomarkers selected from AFP. CA125, CA15-3, CA19-9, CA72-4, CEA, CYFRA 21-1, ProGRP. SCC, and PSA.

In some embodiments, the panel of biomarkers are selected from at least 1, 2, 3, 4, 5, 6, 7, 8, or 9 different biomarkers selected from AFP, CA125, CA15-3, CA19-9, CEA, CYFRA 21-1, ProGRP, SCC, and PSA. In some embodiments, the panel of biomarkers are selected from at least 7 different biomarkers selected from AFP. CA125, CA15-3, CA19-9, CEA, CYFRA 21-1, ProGRP, SCC, and PSA.

In some embodiments, the subject is a male, the panel of biomarkers comprises or consists of AFP, CA125, CA15-3, CA19-9, CEA, CYFRA 21-1, ProGRP, SCC, and PSA.

In some embodiments, the subject is a female, and the panel of biomarkers comprises or consists of AFP. CA125, CA15-3, CA19-9, CEA, CYFRA 21-1, ProGRP, and SCC.

In some embodiments, the panel of biomarkers comprises or consists of AFP, CA125, CA15-3, CA19-9, CA72-4, CEA, and CYFRA 21-1. In some embodiments, the panel of biomarkers comprises or consists of AFP, CA125, CA15-3, CA19-9, CA72-4, CEA, CYFRA 21-1, ProGRP, SCC, and PSA.

In some embodiments, the panel of biomarkers comprises or consists of CEA, CYFRA 21-1, SCC, and ProGRP.

In some embodiments, the method comprises storing a set of data comprising records from more than 2000, 3000, 4000, 5000, 6000, 7000, 8000, 9000, or 10000 subjects. In some embodiments, the classifier comprises applying Generalized Linear Model (GLM), Gradient Boosting Machine (GBM), Random Forest (RF), and Support Vector Machine (SVM) to the set of data comprising a plurality of clinical records. In some embodiments, the classifier further comprises applying GLM to integrating the cancer predicting score from Generalized Linear Model (GLM), Gradient Boosting Machine (GBM), Random Forest (RF), and Support Vector Machine (SVM).

In one aspect, the disclosure provides a computer implemented method of determining whether to treat a post-surgery patient, the method comprising: (a) quantifying the level of a panel of biomarkers from the blood sample of the patient, wherein the panel of biomarkers comprises at least 1, 2, 3, 4, 5, 6, 7, 8, or 9 (e.g., at least 7) biomarkers selected from AFP, CA125, CA15-3, CA19-9, CEA, CYFRA 21-1, ProGRP, SCC, and PSA; (b) selecting a plurality of parameters for inputs into a machine learning system, wherein the plurality of parameters comprises the level of the panel of biomarkers; (c) training the machine learning system using a machine learning algorithm selected from the group consisting of Generalized Linear Model (GLM), Gradient Boosting Machine (GBM), Random Forest (RF), and Support Vector Machine (SVM); and (d) determining a cancer predicting score, wherein a high cancer predicting score (e.g., greater than 0.9) indicates that the patient should be treated after surgery, and a low cancer predicting score (e.g., not greater than 0.9) indicates that no treatment is needed for the patient.

In some embodiments, the patient is a male, and the panel of biomarkers comprises or consists of AFP. CA125, CA15-3, CA19-9, CEA, CYFRA 21-1, ProGRP, SCC, and PSA. In some embodiments, the patient is a female, and the panel of biomarkers comprises or consists of AFP, CA125, CA15-3, CA19-9, CEA, CYFRA 21-1. ProGRP, and SCC. In some embodiments, the panel of biomarkers comprises or consists of AFP, CA125, CA15-3, CA19-9, CA72-4, CEA, and CYFRA 21-1. In some embodiments, the panel of biomarkers comprises or consists of AFP. CA125, CA15-3, CA19-9, CEA, CYFRA 21-1, ProGRP, SCC, and PSA.

In some embodiments, the panel of biomarkers comprises or consists of CEA, CYFRA 21-1, SCC, and ProGRP.

In one aspect, the disclosure provides a computer implemented method for early detection of the degree of abnormality in a blood sample in a subject, the method comprising: (a) quantifying the level of a panel of biomarkers from the blood sample of the subject, wherein the panel of biomarkers comprises at least 1, 2, 3, 4, 5, 6, 7, 8, or 9 (e.g., at least 7) biomarkers selected from AFP, CA125, CA15-3, CA19-9, CEA, CYFRA 21-1, ProGRP, SCC, and PSA; (b) selecting a plurality of parameters for inputs into a machine learning system, wherein the plurality of parameters comprises the level of the panel of biomarkers; (c) training the machine learning system using at least two machine learning algorithms selected from the group consisting of Generalized Linear Model (GLM), Gradient Boosting Machine (GBM), Random Forest (RF), and Support Vector Machine (SVM), and applying GLM to the results from the at least two machine learning algorithms; and (d) determining a cancer signal score, wherein a high cancer signal score indicates a high degree of abnormality in the blood sample.

In some embodiments, the patient is a male, and the panel of biomarkers comprises or consists of AFP, CA125, CA15-3, CA19-9, CEA, CYFRA 21-1, ProGRP, SCC, and PSA. In some embodiments, the patient is a female, and the panel of biomarkers comprises or consists of AFP, CA125, CA15-3, CA19-9, CEA, CYFRA 21-1, ProGRP, and SCC. In some embodiments, the panel of biomarkers comprises or consists of AFP, CA125, CA15-3, CA19-9, CA72-4, CEA, and CYFRA 21-1. In some embodiments, the panel of biomarkers comprises or consists of AFP, CA125, CA15-3, CA19-9, CEA, CYFRA 21-1, ProGRP, SCC, and PSA.

In some embodiments, the panel of biomarkers comprises or consists of CEA, CYFRA 21-1, SCC, and ProGRP.

In some embodiments, the method is a computer-implemented method.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 4 shows the sensitivity and specificity trend when the number of PTMs increased using the conventional clinical method. The performance of a different number of PTMs was evaluated. When only one PTM is tested, the sensitivity is low, but the specificity is high. In contrast, the sensitivity increases, and specificity decreases when the number of PTMs is increased. PTMs, protein tumor markers.

FIG. 5 is a table showing the comparison of performance between the conventional clinical method and AI method.

FIGS. 6A-6C show the performance of MCED model by GLM. (A) The receiver operating characteristic (ROC) curve evaluated the performance of GLM MCED model in the training and independent validation cohorts. The area under the curve (AUC) of the three cohorts was depicted in FIG. 6A. The dotted vertical line in the ROC in FIG. 6A represents a 90.0% specificity. (B) The sensitivity of GLM MCED model in individual tumor types. Sensitivity (y-axis) by cancer class based on individual cancer classes (x-axis), including multiple cancer types. Cancer classes are ordered based on sensitivity reducing, bars indicate 95% CI. The numbers in parentheses indicate the samples for each cancer class. (C) The sensitivity of GLM MCED model in each clinical stage. Sensitivity (y-axis) based on individual cancer stage (x-axis), bars indicate 95% CI. The numbers in parentheses indicate the samples for each clinical stage.

DETAILED DESCRIPTION

Figure 1:
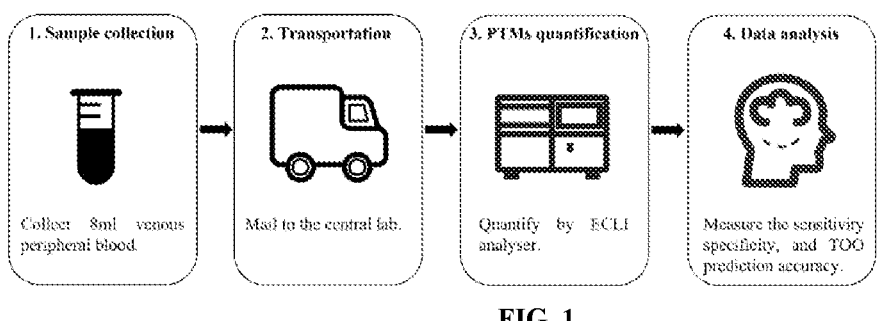
FIG. 1 shows a schematic representation of clinical implementation workflow of sample test. 8 ml peripheral blood sample was collected from the individual in a cell-free DNA blood collection tube and mailed to the central lab. This is a special tube that proteins are stabilized stored at room temperature for seven days which makes it remote accessible as long as there's a local nurse who can draw blood. After plasma separation by centrifugation in the lab, PTM levels were measured by an electrochemiluminescence immunoassay analyzer. MCED was established using AI to distinguish cancer from non-cancer individuals by calculating the probability of cancer (POC) index based on the plasma levels of selected PTMs and clinical information including sex and age of the individuals. Then using another model to predict the possible affected TOO who has been detected with a cancer signal. PTMs, protein tumor markers. ECLI, electrochemiluminescence immunoassay. TOO, tissue of origin.

Cancer is an important public health issue worldwide. The global cancer burden is increasing rapidly, and nearly 19.3 million new cases and 10.0 million cancer deaths were estimated in 2020. It is estimated that more than two-thirds of annual cancer deaths in the world occur in LMICs. The global cancer burden is expected to be 28.4 million cases in 2040, a 47% rise from 2020, with a larger increase in transitioning (64% to 95%) versus transitioned (32% to 56%) countries due to demographic changes, although this may be further exacerbated by increasing risk factors associated with limited medical infrastructure in LMICs. It is well acknowledged that cancer early detection offers a higher cure rate and 5-year survival rate as well as a reduction in treatment cost and loss of economic productivity. Various cancer screening techniques are currently available in clinical practice. Examples include low-dose computed tomography (LDCT) for lung cancer screening, mammogram used to detect breast cancer, HPV test or cytology combined with colposcopy for early detection of cervical cancer, faecal occult blood test (FOBT) combined with colonoscopy for colorectal cancer screening, and prostate-specific antigen (PSA) for prostate cancer. However, the high cost of these screening methods and their need for specialised infrastructure and skilled technicists limit their application, and this is why there are alternatives of screening tests in LMICs: visual inspection with acetic acid (VIA) for cervical cancer and clinical breast examination (CBE) for breast cancer screening. Moreover, these methods are individually designed for screening for specific cancer types, hindering their widespread use as screening tools. In addition, liquid biopsy methods, which detect blood-based analytes such as cancer-derived DNA, are now being adopted in human medicine to simultaneously screen for multiple types of cancer; these MCED tests represent a paradigm shift in cancer screening and promise to significantly increase the number of patients with cancer that are detected at earlier stages. However, these tests are not suitable for using in LMICs due to cost, complexity, and dependency on high-end infrastructure and a rigorous laboratory. Taken together, these factors contribute to the fact that cancer is often diagnosed at a later stage and to inequalities in health care. In order to perform large-scale cancer screening among apparently healthy individuals in the future, especially among the population in LMICs, the development and validation of a more general, robust, and affordable MCED test are essential.

Immunological measurement of blood-based PTMs has been performed over decades in clinical for cancer screening of apparently healthy individuals on large-scale; for example, alpha-fetoprotein (AFP) for liver cancer, CA125 for ovarian cancer, CA15-3 for breast cancer, CA19-9 for pancreatic cancer, CA72-4 for ovarian cancer, carcinoembryonic antigen (CEA) for cancers in digestive tract, and CYFRA 21-1 for breast carcinoma. Such methods have significant advantages including their non-invasive nature, automation, and relatively low cost compared with many other clinical detection methods (endoscopy, imaging, etc.). However, the low sensitivity of these methods for early cancer detection limits their widespread use for screening purposes in a general population setting.

Previous studies have shown that PTM panels are diagnostically superior to single marker for the early detection of colorectal cancer, lung cancer, breast cancer, liver cancer, gastric cancer, pancreatic cancer, ovarian cancer, and oesophagus cancer. Several reports have also demonstrated that a combined PTM panel could be used for detecting several cancer types at the same time. However, different cancer types normally show different serological characteristics. Test results can also become more complex as the sample size increases, and traditional statistical methods may not be able to handle such big data. In addition, conventional clinical methods detect multiple PTMs at the same time and use a single threshold to evaluate the results, which may cause the accumulation of false-positive rates and lead to unnecessary clinical diagnostic workups. Hence, they were not suitable for asymptomatic large-scale population screening. AI is a good analytical method for solving classification challenges by identifying implicit patterns from complex data. Over the last decade, the significant contribution of AI techniques to this advanced technology has played a critical role in medicine and healthcare research. AI is considered a valuable tool in transforming the future of healthcare and precision oncology. Several novel algorithms have shown promising results for the accurate detection and characterisation of suspected lesions.

Implementations of the disclosure provide techniques for developing a machine learning system for multi-cancer early detection (MCED) tests to identify more than one type of cancer from a single blood sample with high sensitivity and high accuracy. The machine learning system can be trained by one or more machine learning algorithms to distinguish cancer from non-cancer individuals and identify tissue of origin (TOO) in a cancer patient.

This disclosure is based on, in part, the observational study that comprises a retrospective analysis on the data generated from the routine clinical testings. 7565 participants (954 with cancer and 6611 without) were divided into training and independent validation cohort. A second validation cohort (1005 with cancer and 812 without) was also tested. Patients with cancer prior to therapy were eligible for inclusion in the study. Individuals with no history of cancer were enrolled from the participating sites as the non-cancer group. One tube of peripheral blood was collected from each participant and quantified a panel of selected protein tumor markers (PTMs) by a common clinical electrochemiluminescence immunoassay analyzer. An algorithm was established using artificial intelligence (AI) to distinguish cancer patients from non-cancer individuals by calculating the probability of cancer (POC) index based on the quantification results of the selected PTMs and clinical information including sex and age of the individuals and to predict the possible affected tissue of origin (TOO) for those who have been detected with cancer signals in blood.

Different types of cancer require specific panels of PTMs, which can be used for cancer screening. However, relying solely on a single threshold for each PTM in conventional clinical methods presents challenges when combining results of multiple PTMs, leading to an accumulation of false positives as the number of markers increases. Nevertheless, in some embodiments, the machine learning system is trained with one or more machine learning algorithms to process data for multiple cancer types together to distinguish cancer from non-cancer individuals by calculating the probability of cancer (POC) index based on the expression of multiple PTMs and clinical basic information including sex and age of the individuals. By integrating multiple conventional clinical tests into a single one, it significantly reduces false positive rates, while maintaining the combined sensitivity of multiple tests and eliminating differences in PTMs levels among demographic groups, such as various age groups and genders. Thus, this method provides the simultaneous detection of multiple cancer types with good performance. The trained machine learning system can be also used to identify tissue of origin (TOO) in a cancer patient. Upon determination of whether a subject is likely to have cancer and/or identification of the TOO in a cancer patient using the machine learning system, the machine learning system can be used to treat a cancer in a subject, monitor the progression of the disease, determine the effectiveness of the treatment, and adjust treatment strategy. The computer-implemented method enables early detection of cancer and more timely evaluation of treatment effectiveness, thereby reducing the likelihood of missing the optimal treatment window and lowering cancer mortality rates, ultimately improving the quality of life for cancer patients. The computer-implemented method described herein was empowered by AI technology to significantly reduce the false positive rate, increasing the specificity from 56.9% (95% confidence interval (CI): 55.8% to 58.0%) to 92.9% (95% CI: 92.3% to 93.5%). In all cancer types, the overall sensitivity was 51.7% (95% CI: 49.4% to 53.9%), resulting in 84.3% (95% CI: 83.5% to 85.0%) accuracy. The performance was generally consistent in the training and the two validation cohorts. The sensitivities ranged from 37.1% to 77.6% for the detection of the nine common cancer types (including e.g., breast, colorectum, liver, lung, lymphoma, oesophagus, ovary, pancreas, and stomach), which account for ~59.2% of global cancer deaths annually. Furthermore, it has shown excellent sensitivity in several high-mortality cancer types for which routine screening tests are lacking in the clinic, such as the sensitivity of pancreatic cancer which was 77.6% (95% CI: 69.3% to 84.6%). The overall accuracy of tissue of origin (TOO) prediction in the true positives was 66.8%, which could assist the clinical diagnostic workup.

The method described herein significantly outperforms the conventional clinical method, representing a novel blood-based test for multi-cancer early detection (MCED) which is non-invasive, easy, efficient, and robust. Moreover, the accuracy of TOO facilitates the follow-up diagnostic workup. In addition, the method described herein is affordable (less than $25) and accessible requiring nothing more than a blood draw at the screening sites, which makes it acceptable and sustainable in LMICs.

Multi-Cancer Early Detection (MCED) Model

The present disclosure provides a protein assay that integrates the measurement of a panel (e.g., seven or ten) of selected PTMs and clinical information of the individuals, dramatically empowered by AI technology, which is more practical in LMICs (FIG. 1).

In one aspect, the disclosure provides computer-implemented methods for early detection of the presence of cancer in a patient, the computer-implemented method comprising:

(a) quantifying the level of a panel of biomarkers from the blood sample of the patient, wherein the panel of biomarkers comprises at least seven biomarkers selected from AFP, CA125, CA15-3, CA19-9, CA72-4, CEA, CYFRA 21-1, ProGRP, SCC, and PSA;

(b) selecting a plurality of parameters for inputs into a machine learning system, wherein the plurality of parameters comprises the level of the panel of biomarkers;

(c) training the machine learning system using a machine learning algorithm selected from the group consisting of Generalized Linear Model (GLM), Gradient Boosting Machine (GBM), Random Forest (RF), and Support Vector Machine (SVM); and (d) determining a cancer predicting score, wherein a high cancer predicting score indicates a high probability of the patient to have cancer.

In some embodiments, a generalized linear model (GLM) is used. The GLM is a flexible generalization of ordinary linear regression. The GLM generalizes linear regression by allowing the linear model to be related to the response variable via a link function and by allowing the magnitude of the variance of each measurement to be a function of its predicted value. Generalized linear models were formulated as a way of unifying various other statistical models, including linear regression, logistic regression and Poisson regression. In some embodiments, an iteratively reweighted least squares method for maximum likelihood estimation (MLE) of the model parameters is used. MLE remains popular and is the default method on many statistical computing packages. Other approaches, including Bayesian regression and least squares fitting to variance stabilized responses, have been developed.

In some embodiments, the methods described herein involve gradient boosting. Gradient boosting is a machine learning technique used in regression and classification tasks, among others. It gives a prediction model in the form of an ensemble of weak prediction models, which are typically decision trees. In some embodiments, a gradientboosted trees model is built in a stage-wise fashion as in other boosting methods, but it generalizes the other methods by allowing optimization of an arbitrary differentiable loss function.

In some embodiments, the methods described herein involve random forest. Random forests is an ensemble learning method for classification, regression and other tasks that operates by constructing a multitude of decision trees at training time. For classification tasks, the output of the random forest is the class selected by most trees. For regression tasks, the mean or average prediction of the individual trees is returned. Random decision forests correct for decision trees' habit of overfitting to their training set.

In some embodiments, the methods described herein involve support vector machines (SVMs, also support vector networks). SVM are supervised learning models with associated learning algorithms that analyze data for classification and regression analysis. Given a set of training examples, each marked as belonging to one of two categories, an SVM training algorithm builds a model that assigns new examples to one category or the other, making it a non-probabilistic binary linear classifier (although methods such as Platt scaling exist to use SVM in a probabilistic classification setting). SVM maps training examples to points in space so as to maximize the width of the gap between the two categories. New examples are then mapped into that same space and predicted to belong to a category based on which side of the gap they fall. In addition to performing linear classification, SVMs can efficiently perform a non-linear classification using what is called the kernel trick, implicitly mapping their inputs into high-dimensional feature spaces.

In some embodiments, the methods described herein comprises one or more ensemble models by combining models that are trained using different algorithms, parameters, and/or training data to improve overall prediction performance. Instead of relying on a single model, the ensemble models leverage the diversity of multiple models to enhance prediction accuracy and robustness.

In some embodiments, the training data set comprises at least 1000, 2000, 3000, 4000, 5000, 6000, 7000, 8000, 9000, or 10000 subjects. In some embodiments, the true positive cancer patients account for at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80% of the sample size. In some embodiments, the training data set has no more than 1000, 2000, 3000, 4000, 5000, 6000, 7000, 8000, 9000, or 10000 subjects.

In some embodiments, the methods described herein can achieve a sensitivity of at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%. In some embodiments, the sensitivity is about 30% to about 60%, about 30% to about 55%, about 30% to about 50%, about 30% to about 45%, about 30% to about 40%, about 30% to about 35%, about 35% to about 60%, about 35% to about 55%, about 35% to about 50%, about 35% to about 45%, about 35% to about 40%, about 40% to about 60%, about 40% to about 55%, about 40% to about 50%, about 40% to about 45%, about 45% to about 60%, about 45% to about 55%, about 45% to about 50%, about 50% to about 60%, about 50% to about 55%, or about 55% to about 60%.

In some embodiments, the methods described herein can achieve a specificity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95%. In some embodiments, the specificity is about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 55% to about 95%, about 55% to about 90%, about 55% to about 85%, about 55% to about 80%, about 55% to about 75%, about 55% to about 70%, about 55% to about 65%, about 55% to about 60%, about 60% to about 95%, about 60% to about 90%, about 60% to about 85%, about 60% to about 80%, about 60% to about 75%, about 60% to about 70%, about 60% to about 65%, about 65% to about 95%, about 65% to about 90%, about 65% to about 85%, about 65% to about 80%, about 65% to about 75%, about 65% to about 70%, about 70% to about 95%, about 70% to about 90%, about 70% to about 85%, about 70% to about 80%, about 70% to about 75%, about 75% to about 95%, about 75% to about 90%, about 75% to about 85%, about 75% to about 80%, about 80% to about 95%, about 80% to about 90%, about 80% to about 85%, about 85% to about 95%, about 85% to about 90%, or about 90% to about 95%.

In some embodiments, the methods described herein can achieve an accuracy of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90%. In some embodiments, the accuracy is about 50% to about 90%, about 50% to about 85%, about 50% to about 80%, about 50% to about 75%, about 50% to about 70%, about 50% to about 65%, about 50% to about 60%, about 50% to about 55%, about 55% to about 90%, about 55% to about 85%, about 55% to about 80%, about 55% to about 75%, about 55% to about 70%, about 55% to about 65%, about 55% to about 60%, about 60% to about 90%, about 60% to about 85%, about 60% to about 80%, about 60% to about 75%, about 60% to about 70%, about 60% to about 65%, about 65% to about 90%, about 65% to about 85%, about 65% to about 80%, about 65% to about 75%, about 65% to about 70%, about 70% to about 90%, about 70% to about 85%, about 70% to about 80%, about 70% to about 75%, about 75% to about 90%, about 75% to about 85%, about 75% to about 80%, about 80% to about 90%, about 80% to about 85%, or about 85% to about 90%.

In some embodiments, the methods as described herein involves a cross-validation process. In some embodiments, the cross-validation process is a 5-fold, 10-fold, 15-fold, 20-fold, 25-fold, 30-fold, 35-fold, or 40-fold cross-validation process. In some embodiments, the cross-validation process is repeated for at least 10 times, 20 times, 30 times, 40 times, 50 times, or 100 times.

In some embodiments, the methods described herein can reduce the false-positive rate by at least 10%, 20%, 30%, 40%, or 50% as compared to a conventional method to detect cancer, e.g., a method that is based on pre-determined reference ranges for each biomarker.

In addition, in some cases, certain protein biomarkers related to multiple cancer types had a greater contribution or higher weights in the model. Conversely, certain biomarkers that were highly specific to a particular cancer type (e.g., AFP specifically for liver cancer detection) had relatively lower contributions. This led to cases where a highly specific protein biomarker for a certain cancer type exhibited abnormally high level (while others protein markers remained normal), and the MCED model could predict a lower Probability of Cancer (POC) index.

To address this issue, an Outlier Analysis approach was developed to predict these types of cancer patients. The Outlier Analysis method focused on identifying and analyzing cases where a highly specific cancer biomarker showed exceptional expression levels compared to normal cases. By incorporating this approach into the MCED model, the detection of cancer patients who may have exhibited unique biomarker expressions was improved, providing more accurate predictions and insights for multi-cancer early cancer diagnosis. Here, we used the three methods below to determine the cutoff value for outlier analysis, based on more than 6000 non-cancer samples.

1) Box plot method: The box plot method is used to identify outliers by plotting the protein tumor marker expression from normal control samples. A box plot displays the quartile range of the data, and observations that exceed the upper quartile plus 1.5 times the interquartile range can be considered as outliers' cutoff value.

Figure 11:
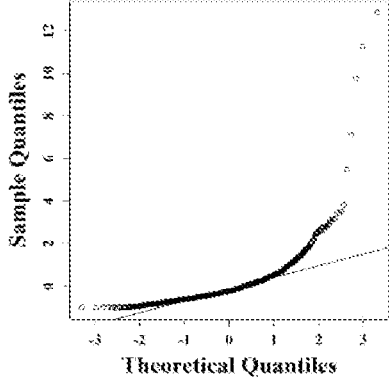
FIG. 11 shows QQ plot of AFP expression from healthy individuals.

2) Modified Z-Score: Since some non-cancer diseases can also result in elevated protein tumor markers expression levels in normal control cohort, the protein expression levels in the normal control cohort exhibit skewness (FIG. 11). Therefore, the modified Z-score is considered the data skewness by calculating the difference between the observation and the median divided by the median absolute deviation (MAD). The expression of protein tumor markers with modified Z-score>10 is defined as outliers' cutoff value.

3) Percentile: The percentile method compares the observation with the percentiles of the data, and observations that exceed the 99th percentile of the normal cohort can be considered as outliers' cutoff value.

Based on the cutoff values obtained from the above three methods, the maximum value is selected as the final abnormal high outliers' cutoff value. If the expression level of a particular biomarker in a test sample is greater than the corresponding abnormal cutoff value, the sample can be predicted as cancer patient. Through the development of this outlier analysis method, we aim to enhance the identification of cancer patients with significantly abnormal level of one cancer specific protein biomarker. By effectively predicting these exceptional cases, we can provide valuable insights into the potential presence of specific types of cancer and aid in early detection.

Thus, in some embodiments, the methods described herein further includes an Outlier Analysis. In some embodiments, the Outlier Analysis described herein involves determining the cutoff value based on at least 1000, 2000, 3000, 4000, 5000, 6000, 7000, 8000, 9000, 10000, 20000, 30000, 40000, or 50000 non-cancer samples. In some embodiments, the cutoff value is determined by selecting the maximum value obtained from the Box plot method, Modified Z-Score, and/or Percentile described herein. In some embodiments, a cutoff value can be determined for each biomarker described herein. In some embodiments, the Outlier Analysis includes comparing the quantified level (e.g., expression level) of a selected biomarker (e.g., any of the biomarkers described herein) to its corresponding cutoff value as determined herein. For example, if the quantified level of the selected biomarker is higher than the corresponding cutoff value, there is a high probability of the patient to have cancer. In some embodiments, the Outlier Analysis is performed by (a) determining a cutoff value for each biomarker (e.g., by Box plot method, Modified Z-Score, and/or Percentile), and (b) comparing the quantified level of each biomarker to its corresponding cutoff value. In some embodiments, a higher quantified level of a biomarker relative to its corresponding cutoff value indicates a high probability of the subject to have cancer.

TOO Prediction

The disclosure provides computer implemented methods for identifying tissue of origin (TOO) in a cancer patient, the method comprising:

(a) quantifying the level of a panel of biomarkers from the blood sample of the patient, wherein the panel of biomarkers are selected from at least 7 biomarkers selected from AFP, CA125, CA15-3, CA19-9, CA72-4, CEA, CYFRA 21-1, ProGRP, SCC, and PSA;

(b) selecting a plurality of parameters for inputs into a machine learning system, wherein the plurality of parameters comprises the level of the panel of biomarkers;

(c) training the machine learning system using Random Forest (RF) or Gradient Boosting Machine (GBM); and (d) determining the TOO based on the machine learning system.

In some embodiments, the methods can achieve an accuracy of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90%. In some embodiments, the accuracy is about 50% to about 90%, about 50% to about 85%, about 50% to about 80%, about 50% to about 75%, about 50% to about 70%, about 50% to about 65%, about 50% to about 60%, about 50% to about 55%, about 55% to about 90%, about 55% to about 85%, about 55% to about 80%, about 55% to about 75%, about 55% to about 70%, about 55% to about 65%, about 55% to about 60%, about 60% to about 90%, about 60% to about 85%, about 60% to about 80%, about 60% to about 75%, about 60% to about 70%, about 60% to about 65%, about 65% to about 90%, about 65% to about 85%, about 65% to about 80%, about 65% to about 75%, about 65% to about 70%, about 70% to about 90%, about 70% to about 85%, about 70% to about 80%, about 70% to about 75%, about 75% to about 90%, about 75% to about 85%, about 75% to about 80%, about 80% to about 90%, about 80% to about 85%, or about 85% to about 90%.

In some embodiments, the sample size of each cancer type is imbalanced, e.g., the proportion of a particular cancer (e.g., any of the cancer types described herein) can be about 1% to about 50%, about 1% to about 40%, about 1% to about 30%, about 1% to about 20%, about 1% to about 10%, about 1% to about 5%, 5% to about 50%, about 5% to about 40%, about 5% to about 30%, about 5% to about 20%, about 5% to about 10%, 10% to about 50%, about 10% to about 40%, about 10% to about 30%, about 10% to about 20%, 20% to about 50%, about 20% to about 40%, about 20% to about 30%, 30% to about 50%, about 30% to about 40%, or about 40% to about 50%.

Measuring Markers in a Sample

As part of the present method, a panel of markers from an asymptomatic human subject may be measured. There are many methods known in the art for measuring either gene expression (e.g., mRNA) or the resulting gene products (e.g., polypeptides or proteins) that can be used in the present methods.

In some embodiments, tumor antigen detection can be conducted using an automated immunoassay analyzer. Representative analyzers include the Elecsys® system from Roche Diagnostics or the Architect® Analyzer from Abbott Diagnostics. In some embodiments, the analyzers used herein include Roche cobas e411/e601 analyzer (Roche Diagnostics GmbH, Mannheim, Germany) and Bioplex 200 platform. Using such standardized platforms permits the results from one laboratory or hospital to be transferable to other laboratories around the world. However, the methods provided herein are not limited to any one assay format or to any particular set of markers that comprise a panel.

The presence and quantification of one or more antigens or antibodies in a test sample can be determined using one or more immunoassays that are known in the art. Immunoassays typically comprise: (a) providing an antibody (or antigen) that specifically binds to the biomarker (namely, an antigen or an antibody); (b) contacting a test sample with the antibody or antigen; and (c) detecting the presence of a complex of the antibody bound to the antigen in the test sample or a complex of the antigen bound to the antibody in the test sample.

Well known immunological binding assays include, for example, an enzyme linked immunosorbent assay (ELISA), which is also known as a "sandwich assay", an enzyme immunoassay (EIA), a radioimmunoassay (RIA), a fluoro-immunoassay (HA), a chemiluminescent immunoassay (CLIA), a counting immunoassay (CIA), a filter media enzyme immunoassay (META), a fluorescence-linked immunosorbent assay (FLISA), agglutination immunoassays and multiplex fluorescent immunoassays (such as the Luminex Lab MAP), immunohistochemistry, etc.

The immunoassay can be used to determine a test amount of an antigen in a sample from a subject. First, a test amount of an antigen in a sample can be detected using the immunoassay methods described above. If an antigen is present in the sample, it will form an antibody-antigen complex with an antibody that specifically binds the antigen under suitable incubation conditions as described herein. The amount, activity, or concentration, etc. of an antibody-antigen complex can be determined by comparing the measured value to a standard or control.

Any methodology that provides for the measurement of a marker or panel of markers from a human subject is contemplated for use with the present methods. In certain embodiments, the sample from the human subject is a tissue section such as from a biopsy. In another embodiment, the sample from the human subject is a bodily fluid such as blood, serum, plasma or a part or fraction thereof. In other embodiments, the sample is a blood or serum and the markers are proteins measured therefrom. In yet another embodiment, the sample is a tissue section and the markers are mRNA expressed therein. Many other combinations of sample forms from the human subjects and the form of the markers are contemplated.

Biomarkers

Before measurement can be performed a panel of markers needs to be selected for a particular cancer being screened. Many markers are known for diseases, including cancers and a known panel can be selected, or as was done as described in the examples. The panel can be selected based on measurement of individual markers in retrospective clinical samples wherein a panel is generated based on empirical data for a desired disease such as cancer, and preferably pancreatic cancer, ovarian cancer, liver cancer, lung cancer, stomach cancer, colorectal cancer, lymphoma, oesophageal cancer, or breast cancer.

Examples of biomarkers that can be employed include molecules detectable, for example, in a body fluid sample, such as, antibodies, antigens, small molecules, proteins, hormones, enzymes, genes and so on. However, the use of tumor antigens has many advantages due to their widespread use over many years and the fact that validated and standardized detection kits are available for many of them for use with the aforementioned automated immunoassay platforms.

In a particular embodiment, a panel of markers is selected based on their association with a particular cancer type. For example, AFP is a specific biomarker for liver cancer. In addition, alpha-fetoprotein (AFP) can be used as a biomarker for liver cancer (e.g., hepatocellular carcinoma), CA125 for ovarian cancer, CA15-3 for breast cancer, CA19-9 for pancreatic cancer, CA72-4 for ovarian cancer, carcinoembryonic antigen (CEA) for cancers in digestive tract, and CYFRA 21-1 for breast carcinoma.

In some embodiments, the panel of biomarkers comprises at least 1, 2, 3, 4, 5, 6, 7, 8, 9 or 10 biomarkers selected from alpha-fetoprotein (AFP), carbohydrate antigen 125 (also known as cancer antigen 125, or CA125), carbohydrate antigen 15-3 (also known as cancer antigen 15-3, or CA15-3), carbohydrate antigen 19-9 (also known as cancer antigen 19-9, CA19-9, sialyl Lewis (a) or sialylated Lewis (a) antigen), carbohydrate antigen 72-4 (also known as cancer antigen 72-4, CA 72-4, or tumor-associated glycoprotein (TAG) 72), carcinoembryonic antigen (CEA), cytokeratin 19 fragments (also known as CYFRA 21-1), pro-gastrin-releasing peptide (ProGRP), squamous cell carcinoma antigen (also known as SCC, SCCA, including SCCA1 and SCCA2), and total prostate-specific antigen (also known as PSA, TPSA, or KLK3).

Among these biomarkers, CA125 is a repeating peptide epitope of the mucin MUC16, which promotes cancer cell proliferation and inhibits anti-cancer immune responses. CA15-3 is derived from glycoprotein Mucin-1 (MUC-1). CA 19-9 is a tumor-associated antigen, which was originally defined by a monoclonal antibody that has been produced by a hybridoma prepared from murine spleen cells immunized with a human colorectal cancer cell line. CA 19-9 exists in tissue as an epitope of sialyated Lewis A blood group antigen. CYFRA 21-1 is a fragment of cytokeratin 19 (KRT19). ProGRP is related to Gastrin-releasing peptide (GRP). GRP is an important regulatory molecule that is implicated in a number of physiological and pathophysiological processes in humans. Its 148 amino acid preproprotein, following cleavage of a signal peptide, is further processed to produce the 27 amino acid GRP and the 68 amino acid ProGRP. Due to its short half-life of 2 minutes, it is not possible to measure GRP in blood. Therefore, an assay for the measurement of ProGRP is useful to study GRP. SCC include SCCA1 (also known as SERPINB3) and SCCA2 (also known as SERPINB4). These biomarkers are known in the art, and are described e.g., Locker, et al. "ASCO 2006 update of recommendations for the use of tumor markers in gastrointestinal cancer." Journal of clinical oncology 24.33 (2006): 5313-5327; Del Villano B C et al: Radioimmunometric assay for a monoclonal antibody-defined tumor marker, CA 19-9. Clin Chem 29: 549, 1983-552; Muraro, Raffaella, et al. "Generation and characterization of B72. 3 second generation monoclonal antibodies reactive with the tumor-associated glycoprotein 72 antigen." Cancer research 48.16 (1988): 4588-4596; each of which is incorporated herein by reference in its entirety.

In some embodiments, a panel of biomarkers in combination with clinical parameters is selected from: AFP, CA125, CA15-3, CA19-9, CA72-4, CEA, CYFRA 21-1. In other embodiments, a panel of biomarkers is selected from AFP, CA125, CA15-3, CA19-9, CA72-4, CEA, CYFRA 21-1, ProGRP, SCC, and PSA. In embodiments, a panel of biomarkers in combination with clinical parameters is selected from: AFP, CA125, CA15-3, CA19-9, CA72-4, CEA, CYFRA 21-1, ProGRP, SCC, and PSA. In other embodiments, a panel of biomarkers is selected from AFP, CA125, CA15-3, CA19-9, CA72-4, CEA, CYFRA 21-1, ProGRP, SCC, and PSA. In some embodiments, clinical parameter can be added, e.g., age, and gender. In some embodiments, the panel of biomarkers are selected from at least 1, 2, 3, 4, 5, 6, 7, 8, 9, or 10 different biomarkers selected from AFP, CA125, CA15-3, CA19-9, CA72-4, CEA, CYFRA 21-1, ProGRP, SCC, and PSA. In some embodiments, the panel of biomarkers are selected from at least 7 different biomarkers selected from AFP, CA125, CA15-3, CA19-9, CA72-4, CEA, CYFRA 21-1, ProGRP, SCC, and PSA.

In some embodiments, the panel of biomarkers comprises or consists of AFP, CA125, CA15-3, CA19-9, CA72-4, CEA, and CYFRA 21-1. In some embodiments, the panel of biomarkers consists of AFP, CA125, CA15-3, CA19-9, CA72-4, CEA, and CYFRA 21-1. In some embodiments, the panel of biomarkers comprises AFP, CA125, CA15-3, CA19-9, CA72-4, CEA, CYFRA 21-1, ProGRP, SCC, and PSA. In some embodiments, the panel of biomarkers consists of AFP, CA125, CA15-3, CA19-9, CA72-4, CEA, CYFRA 21-1, ProGRP, SCC, and PSA.

In some embodiments, the panel of biomarkers are selected from at least 1, 2, 3, 4, 5, 6, 7, 8, or 9 different biomarkers selected from AFP, CA125, CA15-3, CA19-9, CEA, CYFRA 21-1, ProGRP, SCC, and PSA. In some embodiments, the panel of biomarkers are selected from at least 7 different biomarkers selected from AFP, CA125, CA15-3, CA19-9, CEA, CYFRA 21-1, ProGRP, SCC, and PSA.

In some embodiments, the subject is a male, and the panel of biomarkers comprises or consists of AFP, CA125, CA15-3, CA19-9, CEA, CYFRA 21-1, ProGRP, SCC, and PSA.

In some embodiments, the subject is a female, and the panel of biomarkers comprises or consists of AFP, CA125, CA15-3, CA19-9, CEA, CYFRA 21-1, ProGRP, and SCC.

In some embodiments, the panel of biomarkers comprises CEA, CYFRA 21-1, SCC, and ProGRP.

In some embodiments, the panel of biomarkers consists of CEA, CYFRA 21-1, SCC, and ProGRP.

In some embodiments, the panel of biomarkers comprises or consists of CEA, CYFRA 21-1, SCC, and ProGRP and the cancer is lung cancer.

In some embodiments, the panel of biomarkers comprise no more than 1, 2, 3, 4, 5, 6, 7, 8, 9, or 10 different biomarkers.

In some embodiments, the panel of biomarkers consists of 1, 2, 3, 4, 5, 6, 7, 8, 9, or 10 different biomarkers.

In certain embodiments, the panel of markers can comprise markers associated with a cancer selected from pancreatic cancer, ovarian cancer, liver cancer, lung cancer, stomach cancer, colorectal cancer, lymphoma, oesophageal cancer, prostate cancer, or breast cancer.

A panel can comprise any number of markers as a design choice, seeking, for example, to maximize specificity or sensitivity of the assay. Hence, an assay of interest may ask for presence of at least one of two or more biomarkers, three or more biomarkers, four or more biomarkers, five or more biomarkers, six or more biomarkers, seven or more biomarkers, eight or more biomarkers, nine or more biomarkers, ten or more biomarkers, or more as a design choice.

Thus, in one embodiment, the panel of biomarkers may comprise at least two, at least three, at least four, at least five, at least six, at least seven, at least eight, at least nine or at least ten or more different markers. In one embodiment, the panel of biomarkers comprises about two to ten different markers. In another embodiment, the panel of biomarkers comprises about four to eight different markers. In yet another embodiment, the panel of markers comprises about seven different markers. In yet another embodiment, the panel of markers comprises about ten different markers.

Generally, a sample is committed to the assay and the results can be a range of numbers reflecting the presence and level (e.g., concentration, amount, activity, etc.) of presence of each of the biomarkers of the panel in the sample.

Methods of Treatment

The computer-implemented method described herein can further include an additional step of treating a cancer in a subject, more timely evaluating the effectiveness of treatment, reducing the likelihood of missing the optimal treatment window, reducing the rate of the increase of volume of a tumor in a subject over time, reducing the risk of developing a metastasis, and/or reducing the risk of developing an additional metastasis in a subject, upon determination of whether the subject is likely to have cancer and/or identification of the tissue of origin (TOO) in a cancer patient using the machine learning system implemented herein. In some embodiments, the treatment can halt, slow, retard, or inhibit progression of a cancer. In some embodiments, the treatment can result in the reduction of in the number, severity, and/or duration of one or more symptoms of the cancer in a subject. In some embodiments, the compositions and methods disclosed herein can be used for treatment of patients at risk for a cancer.

The treatments can generally include e.g., surgery, chemotherapy, radiation therapy, hormonal therapy, targeted therapy, and/or a combination thereof. Which treatments are used depends on the type, location and grade of the cancer as well as the patient's health and preferences. In some embodiments, the therapy is chemotherapy or chemoradiation.

Figures 14A, 14B:
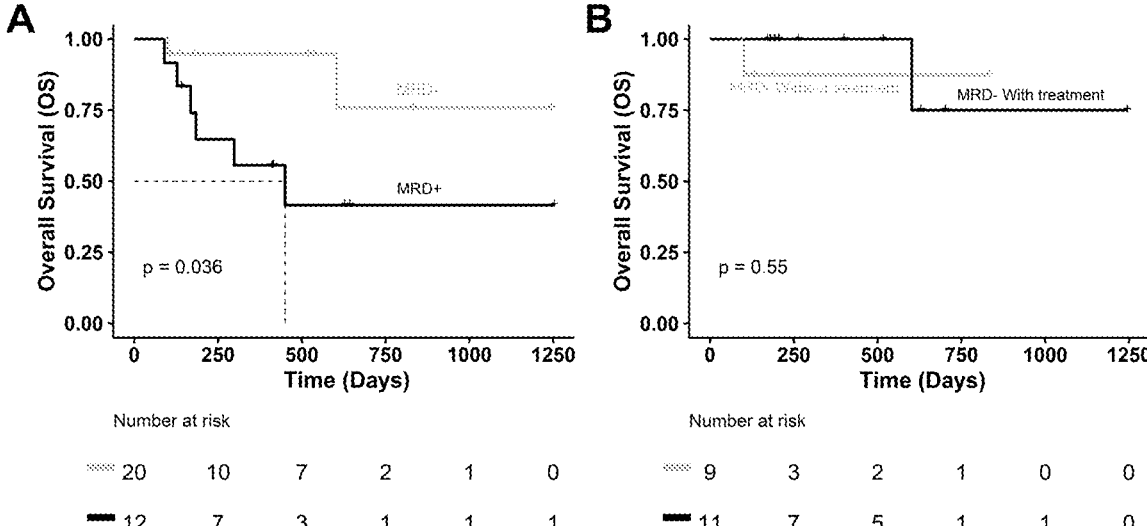
FIGS. 14A-14B show survival analysis result based on MRD status predicted by the Probability of Cancer (POC) index derived from post-surgery blood samples.

In some embodiments, the disclosure is related to methods of determining whether to treat a post-surgery patient. In some embodiments, the methods comprises: (a) quantifying the level of a panel of biomarkers from the blood sample of the patient, wherein the panel of biomarkers comprises at least seven biomarkers selected from AFP, CA125, CA15-3, CA19-9, CA72-4, CEA, CYFRA 21-1, ProGRP, SCC, and PSA (e.g., AFP, CA125, CA15-3, CA19-9, CA72-4, CEA, and CYFRA 21-1); (b) selecting a plurality of parameters for inputs into a machine learning system, wherein the plurality of parameters comprises the level of the panel of biomarkers and/or one or more clinical parameters; (c) training the machine learning system using a machine learning algorithm selected from the group consisting of Generalized Linear Model (GLM), Gradient Boosting Machine (GBM), Random Forest (RF), and Support Vector Machine (SVM); and (d) determining a cancer predicting score, wherein a high cancer predicting score (e.g., great than 0.8, 0.81, 0.82, 0.83, 0.84, 0.85, 0.86, 0.87, 0.88, 0.89, 0.9, 0.91, 0.92, 0.93, 0.94, or 0.95) indicates that the patient should be treated after surgery, and a low cancer predicting score (e.g., no greater than 0.8, 0.81, 0.82, 0.83, 0.84, 0.85, 0.86, 0.87, 0.88, 0.89, 0.9, 0.91, 0.92, 0.93, 0.94, or 0.95) indicates that no treatment is needed for the patient. As discussed in EXAMPLE 6, because no difference in Overall Survival (FIG. 14B) was observed between those who received treatment after surgery and those who did not, there is no need to keep treating post-surgery patients having a low cancer predicting score (MRD−) described herein.

In one aspect, the disclosure features methods that include administering a therapeutically effective amount of a therapeutic agent to the subject in need thereof (e.g., a subject having, or identified or diagnosed as having, a cancer). In some embodiments, the subject has e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has triple-negative breast cancer (TNBC), gastric cancer, urothelial cancer, Merkel-cell carcinoma, or head and neck cancer. In some embodiments, the subject has pancreatic cancer, ovarian cancer, liver cancer, lung cancer, stomach cancer, colorectal cancer, lymphoma, oesophageal cancer, or breast cancer.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the therapeutic agent is to be administered, a severity of symptoms and a route of administration, and thus administration can be determined on an individual basis. An effective amount can be administered in one or more administrations. By way of example, an effective amount is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro.

In some embodiments, the methods described herein can be used to monitor the progression of the disease, determine the effectiveness of the treatment, and adjust treatment strategy. For example, cell free DNA (cfDNA) can be collected from the subject to detect cancer and the information can also be used to select appropriate treatment for the subject. After the subject receives a treatment, cell free DNA can be collected from the subject. The analysis of these cfDNA can be used to monitor the progression of the disease, determine the effectiveness of the treatment, and/or adjust treatment strategy. In some embodiments, the results are then compared to the early results. In some embodiments, a dramatic increase of circulating tumor DNA indicates apoptosis at the tumor cells, which may suggest that the treatment is effective.

In some embodiments, the therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat).

In some embodiments, the therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Rcolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the therapeutic agent is an antibody or antigen-binding fragment thereof. In some embodiments, the therapeutic agent is an antibody that specifically binds to PD-1, CTLA-4, BTLA, PD-L1, CD27, CD28, CD40, CD47, CD137, CD154, TIGIT, TIM-3, GITR, or OX40.

In some embodiments, the therapeutic agent is an anti-PD-1 antibody, an anti-OX40 antibody, an anti-PD-L1 antibody; an anti-PD-L2 antibody; an anti-LAG-3 antibody, an anti-TIGIT antibody, an anti-BTLA antibody, an anti-CTLA-4 antibody, or an anti-GITR antibody.

In some embodiments, the therapeutic agent is an anti-CTLA4 antibody (e.g., ipilimumab), an anti-CD20 antibody (e.g., rituximab), an anti-EGFR antibody (e.g., cetuximab), an anti-CD319 antibody (e.g., clotuzumab), or an anti-PD1 antibody (e.g., nivolumab).

Systems, Software, and Interfaces

The computer-implemented methods described herein (e.g., quantifying, mapping, normalizing, range setting, adjusting, categorizing, counting and/or determining sequence reads, and counts) can be implemented by a computer, processor, software, module or other apparatus. Methods described herein can be computer-implemented methods, and one or more portions of a method sometimes are performed by one or more processors. Embodiments pertaining to methods described herein can be applicable to the same or related processes implemented by instructions in systems, apparatus and computer program products described herein. In some embodiments, processes and methods described herein are performed by automated methods. In some embodiments, an automated method is embodied in software, modules, processors, peripherals and/or an apparatus comprising the like, that determine sequence reads, counts, mapping, mapped sequence tags, elevations, profiles, normalizations, comparisons, range setting, categorization, adjustments, plotting, outcomes, transformations and identifications. As used herein, software refers to computer readable program instructions that, when executed by a processor, perform computer operations, as described herein.

Sequence reads, counts, elevations, and profiles derived from a subject (e.g., a control subject, a patient or a subject is suspected to have tumor) can be analyzed and processed to determine the presence or absence of a genetic variation. Sequence reads and counts sometimes are referred to as "data" or "datasets". In some embodiments, data or datasets can be characterized by one or more features or variables. In some embodiments, the sequencing apparatus is included as part of the system. In some embodiments, a system comprises a computing apparatus and a sequencing apparatus, where the sequencing apparatus is configured to receive physical nucleic acid and generate sequence reads, and the computing apparatus is configured to process the reads from the sequencing apparatus. The computing apparatus sometimes is configured to determine the presence or absence of a genetic variation (e.g., copy number variation, mutations) from the sequence reads.

Implementations of the subject matter and the functional operations described herein can be implemented in digital electronic circuitry, in tangibly-embodied computer software or firmware, in computer hardware, including the structures described herein and their structural equivalents, or in combinations of one or more of the structures. Implementations of the subject matter described herein can be implemented as one or more computer programs, i.e., one or more modules of computer program instructions encoded on a tangible program carrier for execution by, or to control the operation of, a processing device. Alternatively, or in addition, the program instructions can be encoded on a propagated signal that is an artificially generated signal, e.g., a machine-generated electrical, optical, or electromagnetic signal that is generated to encode information for transmission to suitable receiver apparatus for execution by a processing device. A machine-readable medium can be a machine-readable storage device, a machine-readable storage substrate, a random or serial access memory device, or a combination of one or more of them.

Figure 16:
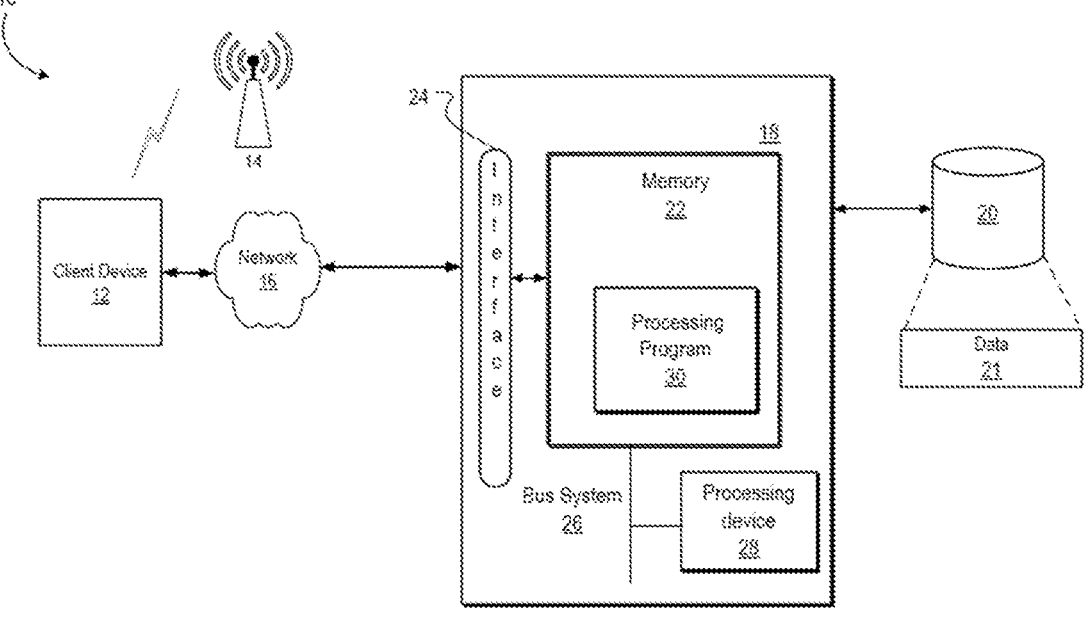
FIG. 16 is a schematic diagram showing a system for implementing the computer-implemented methods as described herein.

Referring to FIG. 16, system 10 processes data via binding data to parameters and applying a sequencing noise processor to the input data, and outputs information (e.g., quality score, Information Score) indicative of sequencing noise. System 10 includes client device 12, data processing system 18, data repository 20, network 16, and wireless device 14. The sequencing noise processor processes the input data based on the computer-implemented methods described herein. In some embodiments, the sequencing noise processor generates a quality score (e.g., information score) based on the computer-implemented methods described herein.

Data processing system 18 retrieves, from data repository 20, data 21 representing one or more values for the sequencing noise processor parameter, including e.g., the nucleotide frequency in control samples, the nucleotide frequency in tumor samples, and the background frequency in the whole human genome, etc. Data processing system 18 inputs the retrieved data into a sequencing noise processor, e.g., into data processing program 30. In this embodiment, data processing program 30 is programmed to detect sequencing noise. In some embodiments, the sequencing noise is detected by calculating information score, Log Odds Product Score, and Log Odds Sum score as described herein.

In some embodiments, data processing system 18 binds to parameter one or more values representing information associated with the variant (e.g., allele frequency at a position of interest). Data processing system 18 binds values of the data to the parameter by modifying a database record such that a value of the parameter is set to be the value of data 21 (or a portion thereof). Data 21 includes a plurality of data records that each have one or more values for the parameter. In some embodiments, data processing system 18 applies data processing program 30 to each of the records by applying data processing program 30 to the bound values for the parameter. Based on application of data processing program 30 to the bound values (e.g., as specified in data 21 or in records in data 21), data processing system 18 determines a score indicating whether the variant is likely to be a true mutation or sequencing noise. In some embodiments, data processing system 18 outputs, e.g., to client device 12 via network 16 and/or wireless device 14, data indicative of the determined quality score, or data indicating whether a variant is a true mutation or sequencing noise.

In some embodiments, based on the data indicating whether a variant is a true mutation or sequencing noise, data processing system 18 can be configured to determine whether a subject has cancer or is at risk of having cancer. If the data processing system 18 determines that the subject has cancer or is at risk of having cancer, data processing system 18 can further update a clinical record in the data 21, indicating the subject has cancer or is at risk of having cancer. In some embodiments, the record includes the need of performing increased monitoring (e.g., increased periodicity of physical examination, and increased frequency of clinic visits), the need for further procedures (e.g., diagnostics, lab tests, or treatment procedures), and recommendation for a lifestyle change.

Data processing system 18 generates data for a graphical user interface that, when rendered on a display device of client device 12, display a visual representation of the output. In some embodiments, the values for these parameters can be stored in data repository 20 or memory 22.

Client device 12 can be any sort of computing device capable of taking input from a user and communicating over network 16 with data processing system 18 and/or with other client devices. Client device 12 can be a mobile device, a desktop computer, a laptop computer, a cell phone, a personal digital assistant (PDA), a server, an embedded computing system, and so forth.

Data processing system 18 can be any of a variety of computing devices capable of receiving data and running one or more services. In some embodiments, data processing system 18 can include a server, a distributed computing system, a desktop computer, a laptop computer, a cell phone, and the like. Data processing system 18 can be a single server or a group of servers that are at a same position or at different positions (i.e., locations). Data processing system 18 and client device 12 can run programs having a client-server relationship to each other. Although distinct modules are shown in the figure, in some embodiments, client and server programs can run on the same device.

Data processing system 18 can receive data from wireless device 14 and/or client device 12 through input/output (I/O) interface 24 and data repository 20. Data repository 20 can store a variety of data values for data processing program 30. The sequencing noise processing program (which may also be referred to as a program, software, a software application, a script, or code) can be written in any form of programming language, including compiled or interpreted languages, or declarative or procedural languages, and it can be deployed in any form, including as a stand-alone program or as a module, component, subroutine, or other unit suitable for use in a computing environment. The data processing program may, but need not, correspond to a file in a file system. The program can be stored in a portion of a file that holds other programs or information (e.g., one or more scripts stored in a markup language document), in a single file dedicated to the program in question, or in multiple coordinated files (e.g., files that store one or more modules, sub programs, or portions of code). The data processing program can be deployed to be executed on one computer or on multiple computers that are located at one site or distributed across multiple sites and interconnected by a communication network.

In some embodiments, data repository 20 stores data 21 indicative of sequencing reads of samples from control subjects and sequencing reads of samples from tumor patients or patients who are suspected to have tumor. In another embodiment, data repository 20 stores parameters of the sequencing noise processor. Interface 24 can be a type of interface capable of receiving data over a network, including, e.g., an Ethernet interface, a wireless networking interface, a fiber-optic networking interface, a modem, and so forth. Data processing system 18 also includes a processing device 28. As used herein, a "processing device" encompasses all kinds of apparatuses, devices, and machines for processing information, such as a programmable processor, a computer, or multiple processors or computers. The apparatus can include special purpose logic circuitry, e.g., an FPGA (field programmable gate array) or an ASIC (application specific integrated circuit) or RISC (reduced instruction set circuit). The apparatus can also include, in addition to hardware, code that creates an execution environment for the computer program in question, e.g., code that constitutes processor firmware, a protocol stack, an information base management system, an operating system, or a combination of one or more of them.

Data processing system 18 also includes a memory 22 and a bus system 26, including, for example, a data bus and a motherboard, which can be used to establish and to control data communication between the components of data processing system 18. Processing device 28 can include one or more microprocessors. Generally, processing device 28 can include an appropriate processor and/or logic that is capable of receiving and storing data, and of communicating over a network. Memory 22 can include a hard drive and a random access memory storage device, including, e.g., a dynamic random access memory, or other types of non-transitory, machine-readable storage devices. Memory 22 stores data processing program 30 that is executable by processing device 28. These computer programs may include a data engine for implementing the operations and/or the techniques described herein. The data engine can be implemented in software running on a computer device, hardware or a combination of software and hardware.

Various methods and formulae can be implemented, in the form of computer program instructions, and executed by a processing device. Suitable programming languages for expressing the program instructions include, but are not limited to, C, C++, an embodiment of FORTRAN such as FORTRAN77 or FORTRAN90, Java, Visual Basic, Perl, Tcl/Tk, JavaScript, ADA, and statistical analysis software, such as SAS, R, MATLAB, SPSS, and Stata etc. Various aspects of the computer-implemented methods may be written in different computing languages from one another, and the various aspects are caused to communicate with one another by appropriate system-level-tools available on a given system.

The processes and logic flows described in this disclosure can be performed by one or more programmable computers executing one or more computer programs to perform functions by operating on input information and generating output. The processes and logic flows can also be performed by, and apparatus can also be implemented as, special purpose logic circuitry, e.g., an FPGA (field programmable gate array) or an ASIC (application specific integrated circuit) or RISC.

Computers suitable for the execution of a computer program include, by way of example, general or special purpose microprocessors, or both, or any other kind of central processing unit. Generally, a central processing unit will receive instructions and information from a read only memory or a random access memory or both. The essential elements of a computer are a central processing unit for performing or executing instructions and one or more memory devices for storing instructions and information. Generally, a computer will also include, or be operatively coupled to receive information from or transfer information to, or both, one or more mass storage devices for storing information, e.g., magnetic, magneto optical disks, or optical disks. However, a computer need not have such devices. Moreover, a computer can be embedded in another device, e.g., a mobile telephone, a smartphone or a tablet, a touchscreen device or surface, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and information include various forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and (Blue Ray) DVD-ROM disks. The processor and the memory can be supplemented by, or incorporated in, special purpose logic circuitry.

To provide for interaction with a user, implementations of the subject matter described in this disclosure can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well. In addition, a computer can interact with a user by sending documents to and receiving documents from a device that is used by the user; for example, by sending web pages to a web browser on a user's client device in response to requests received from the web browser.

Implementations of the subject matter described herein can be implemented in a computing system that includes a back end component, e.g., as an information server, or that includes a middleware component, e.g., an application server, or that includes a front end component, e.g., a client computer having a graphical user interface or a Web browser through which a user can interact with an implementation of the subject matter, or any combination of one or more such back end, middleware, or front end components. The components of the system can be interconnected by any form or medium of digital information communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, the server can be in the cloud via cloud computing services.

While this disclosure includes many specific implementation details, these should not be construed as limitations on the scope of any of what may be claimed, but rather as descriptions of features that may be specific to particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are described in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. In one embodiment, the processes depicted in the accompanying figures do not necessarily require the particular order shown, or sequential order, to achieve desirable results. In some implementations, multitasking and parallel processing may be advantageous.

Kits

The present disclosure also provides kits for collecting, transporting, and/or analyzing samples. Such a kit can include materials and reagents required for obtaining an appropriate sample from a subject, or for measuring the levels of particular biomarkers. In some embodiments, the kits include those materials and reagents that would be required for obtaining and storing a sample from a subject. The sample is then shipped to a service center for further processing (e.g., sequencing and/or data analysis).

The kits may further include instructions for collect the samples, performing the assay and methods for interpreting and analyzing the data resulting from the performance of the assay.

EXAMPLES

The invention is further described in the following examples, which do not limit the scope of the invention described in the claims.

Example 1: A Panel of Seven Protein Tumor Markers for Effective and Affordable Multi-Cancer Early Detection by Artificial Intelligence: A Large-Scale and Multicenter Case-Control Study (1) Methods The following materials and methods were used in the following examples.

Participants 591 patients with cancer and 1055 non-cancer individuals were recruited as SeekIn laboratory-developed test (training cohort). The concentrations of PTMs from 363 patients with cancer and 5556 non-cancer individuals were collected from a partner hospital as independent validation cohort 1. Eligible patients with cancer were diagnosed with pathological confirmation and treatment-naïve prior to blood draw. Non-cancer individuals had no history of cancer. Cancer participants were also excluded for a prior diagnosis of cancer. Clinical data and PTMs quantification data of 1005 patients with cancer and 812 non-cancer individuals previously published by Cohen et al. were included as independent validation cohort 2 for analysis in this study.

Quantification of PTMs

Peripheral blood was collected using a serum collection tube (BD Biosciences, San Jose, USA). Serum was separated within 4~6 hours using a centrifuge at 1300×g for 10 minutes at 4° C. Samples from SeekIn were collected using a Cell-Free DNA BCT (Streck, La Vista, USA). Plasma samples were separated by centrifugation at 1600×g for 10 minutes at 4° C. within 3~5 days. A total of 500 μL of plasma or serum from each blood sample was used to measure the levels of seven designated PTMs, including AFP, CA125, CA15-3, CA19-9, CA72-4, CEA, and CYFRA 21-1, using Roche cobas e411/e601 analyzer (Roche Diagnostics GmbH, Mannheim, Germany) and commercially available reagent kits following manufacturer's instructions. The cut-off values for each biomarker were as follows: 5.8 IU/ml for AFP, 35.0 U/ml for CA125, 26.4 U/ml for CA15-3, 27.0 U/ml for CA19-9, 6.9 U/ml for CA72-4, 4.7 ng/ml for CEA, and 3.3 ng/ml for CYFRA21-1, as recommended by the manufacturer, which is set in advance based on a large-scale normal population. This test was calibrated as per the manufacturer's instructions using a two-point calibration, and quality control was performed. Plasma samples of independent validation cohort 2 from Johns Hopkins University School of Medicine used the Bioplex 200 platform (Bio-Rad, Hercules CA) for quantification of only six PTMs without CA72-4.

Building Cancer Detection Models

Figures 2A, 2B, 2C:
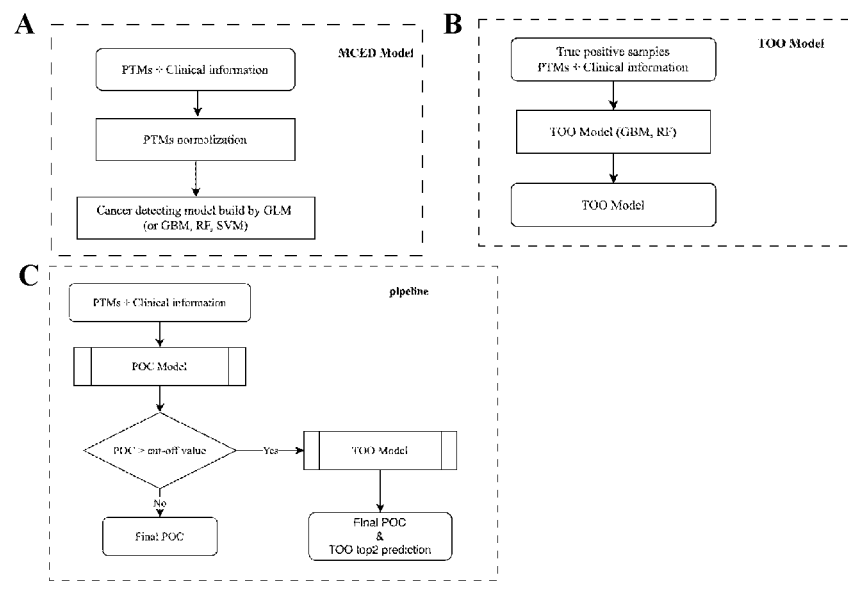
FIGS. 2A-2B show the process of multi-cancer early detection (MCED) model and TOO model. GBM, Gradient Boosting Machine. GLM, Generalized Linear Model. RF, Random Forest. SVM, Support Vector Machine. TOO, tissue of origin. +, means prediction positive case.
FIG. 2C shows the process of MCED pipeline for one test sample.

The study utilized seven protein markers and two clinical characteristics (age and sex) as input features for an AI algorithm. The first step is the development and validation of the cancer detection model. Different AI methods, including Gradient Boosting Machine (GBM), Generalized Linear Model (GLM), Random Forest (RF), and Support Vector Machine (SVM), were employed to create the model that could differentiate between cancer and non-cancer individuals. For the assessments, we compared the area under the curve (AUC) values and sensitivity/specificity of different models by the R package "pROC (1.18.0)". For example, the GLM algorithm was chosen to establish the model to distinguish cancer from non-cancer individuals (FIG. 2A). The final model was built using GLM and 10-fold cross-validation was repeated 30 times. The average prediction value from these GLM models was defined as the probability of cancer (POC). POC value at 90.0% specificity was selected as cut-off value. When the test result was greater than cut-off, it indicated that cancer signals were detected. Otherwise, no cancer signal was detected (FIGS. 2B-2C).

(2) Results

Study Design and Participants' Demographic Characteristics

Between November 2012 and May 2022, 7565 participants were enrolled at SeekIn and partner hospital. Samples were divided into training (n=1646, the samples from SeekIn) and independent validation cohort 1 (n=5919, the samples from a partner hospital). Independent validation cohort 2 (n=1817) was from Johns Hopkins University School of Medicine published data. The cancer group included 496 cases of colorectal cancer, 300 cases of lung cancer, 291 cases of breast cancer, 244 cases of liver cancer, 159 cases of lymphoma, 149 cases of stomach cancer, 125 cases of pancreatic cancer, 82 cases of ovarian cancer, 66 cases of oesophageal cancer and 47 cases of cancers of the other origins. It should be noted that the selection of these cancer patients was not random, and there might be potential bias across different cancer types. As a case-control study to evaluate an MCED test, we intentionally selected the cancer types which were prevalent globally.

Figures 3A, 3B:
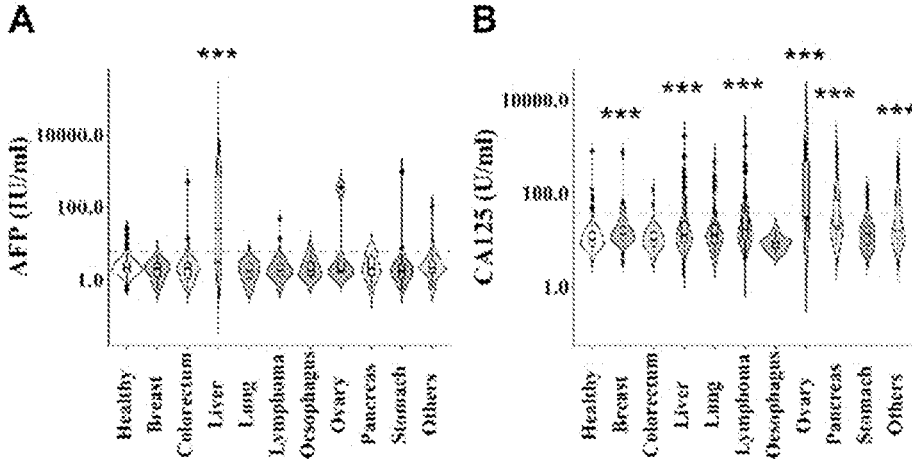
FIGS. 3A-3B show quantification of AFP and CA125 in different cancer types. Quantification value of each PTM (y-axis) based on healthy or individual cancer types (x-axis). The black horizontal lines are cut-off values that are recommended by the manufacturer.  indicates P-value<0.01, * indicates P-value<0.001.

The Performance of the Conventional Clinical Method for Cancer Detection Based on the PTMs Except for the samples from the partner hospital, which were serum, the other two cohorts had plasma samples. The training set and independent validation cohort 1 were using Roche cobas analyzers, while the third cohort from Johns Hopkins University School of Medicine published data used the Bioplex 200 platform. Considering that the data from Johns Hopkins University only contained six tumor markers and lacked the value of CA72-4, we used the mean value of CA72-4 from the non-cancer sample group in the training cohort to replace the missing value. The values of these PTMs (AFP, CA125) for the training cohort are shown in FIGS. 3A-3B. In addition, when a single tumor marker was analyzed, the specificity was high, while multiple tumor markers were analyzed according to the conventional clinical method, and the false-positive rate was cumulative. The conventional clinical method mentioned here is a method based on the quantification of PTMs and assesses the results merely by a single threshold, which is based on pre-determined reference ranges for each PTM recommended by the manufacturer (i.e., the manufacturer-suggested cut-off value (MSCV)). The sensitivity elevated when the number of PTMs increased in the conventional clinical method but, as a trade-off, the specificity decreased at the same time (FIG. 4). The data in FIG. 5 showed that simultaneous detection of these seven PTMs in all samples, the specificity was only 56.9% (95% CI: 55.8% to 58.0%). Taken together, these results indicated that the conventional clinical method using multiple tumor marker panels has a very high false-positive rate.

Figures 6B, 6C:
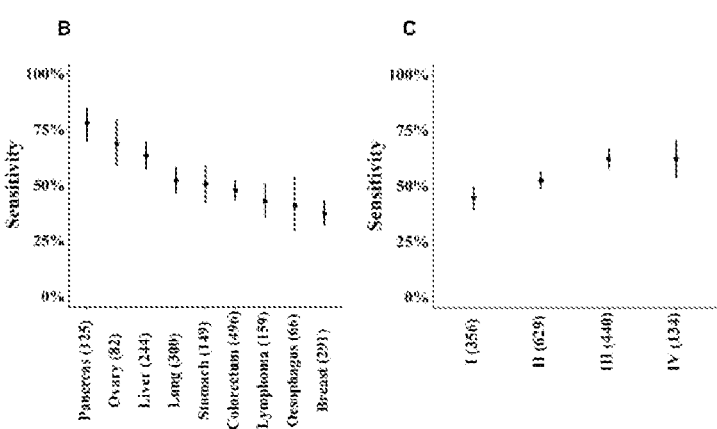

The Performance Characteristics Comparison Between AI Method and the Conventional Clinical Method Considering the high false-positive rate of the conventional clinical method, a highly specific and robust MCED method is very essential in clinic. An algorithm was established using AI to distinguish cancer from non-cancer individuals by calculating the probability of cancer (POC) index based on the expression of the seven PTMs and clinical basic information including sex and age of the individuals. The GLM algorithm was chosen to establish the MCED model, which could distinguish cancer from non-cancer controls in the training (AUC=0.868) and the two independent validation cohorts (AUC=0.744 and 0.818, respectively; FIG. 6A). With the specificity at ~90.0%, the sensitivity across these three cohorts was 58.2% (training cohort, 95% CI: 54.1% to 62.2%), 47.4% (independent validation cohort 1, 95% CI: 42.1% to 52.7%), and 49.3% (independent validation cohort 2, 95% CI: 46.1% to 52.4%), respectively. Among these tumor types, pancreas had the highest sensitivity of 77.6% (95% CI: 69.3% to 84.6%), followed by ovary (68.3% (95% CI: 58.5% to 79.5%)), liver (63.1% (95% CI: 56.7% to 69.2%)), lung (52.0% (95% CI: 46.2% to 57.8%)), stomach (50.3% (95% CI: 42.0% to 58.6%)), colorectum (47.4% (95% CI: 42.9% to 51.9%)), lymphoma (42.8% (95% CI: 35.0% to 50.8%)), oesophagus (40.9% (95% CI: 29.0% to 53.7%)), and breast (37.1% (95% CI: 31.5% to 42.9%)). The sensitivity basically increased with increasing clinical stage (stage I (n=356), 44.4% (95% CI: 39.1% to 49.7%); stage II (n=629), 52.5% (95% CI: 48.5% to 56.4%); stage III (n=440), 62.0% (95% CI: 57.3% to 66.6%); stage IV (n=134), 61.9% (95% CI: 53.2% to 70.2%)). The sensitivities of GLM MCED model in individual tumor types and each cancer stage are depicted in FIGS. 6B-6C.

Example 2: Building Cancer Prediction Models Using Different AI Methods

Figure 7:
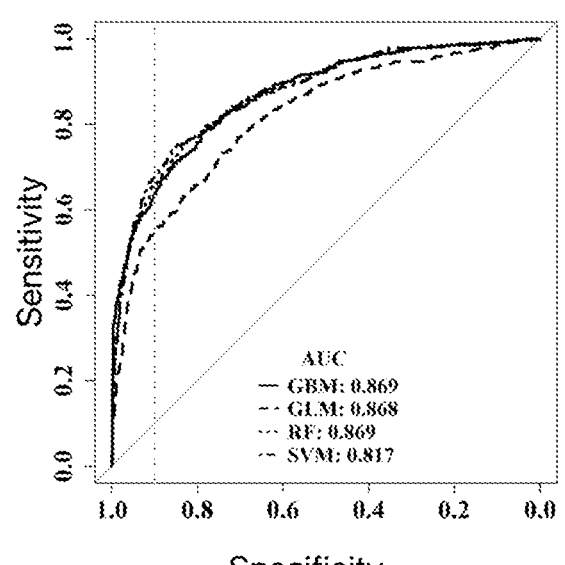
FIG. 7 show performance of different AI algorithms used in the model. The receiver operating characteristic (ROC) curve evaluates the performance of different algorithms in the training cohort. The area under the curve (AUC) was depicted in the figure. The dotted vertical line in the ROC figure represents a 90.0% specificity. GBM, Gradient Boosting Machine. GLM, Generalized Linear Model. RF, Random Forest. SVM, Support Vector Machine.

The same analysis was performed as described in EXAMPLE 1. However, we chose different AI methods to build the cancer prediction model, such as GBM, RF, and SVM. The results are shown in FIG. 7. Compared with GLM (AUC=0.868), the AUC values of GBM, RF and SVM were 0.869, 0.869 and 0.817, respectively. Thus, the results indicate that GBM and RF algorithms have a similar performance as compared to GLM.

Example 3: Predicting Affected TOO

Most liquid biopsies are unable to identify affected TOO in patients who test positive, especially those based on genetic mutations, because the same gene mutations drive multiple tumor types. However, a critical attribute of a blood-based multi-cancer detection test is the ability to localize the TOO to direct the diagnostic workup. Based on the tissue-specific characteristics of PTMs, we used supervised AI algorithm to predict the underlying cancer type in patients with true positive tests (FIG. 2B).

For the prediction of TOO, the true positive cancer patients of three cohorts were used to develop the TOO model by machine learning method (such as RF, GBM). If the sample size of each cancer type is imbalanced, for example, the proportion of lung cancer in the true positive cohort was 40%, however that of lymphoma was less 5%. The downsampling method or upweighting method was employed to balance sample size of each cancer type. The top two organs with the highest prediction probability were considered as the potential TOO.

Figure 8:
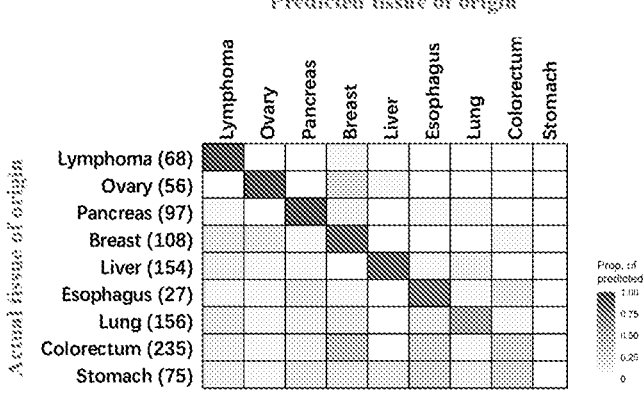
FIG. 8 shows TOO accuracy by individual cancer type. Confusion matrices representing the accuracy of TOO localization. Agreement between the actual (x-axis) and predicted (y-axis) TOO per sample using the GLM MCED model was depicted. Color corresponds to the proportion of predicted TOO calls. Included 976 participants were those with cancer predicted as having cancer at 92.9% specificity.

We then used the method of EXAMPLE 1 to study 976 patients with cancer scoring true positives from these three cohorts in the multi-cancer detection test to predict the possible affected organ system (FIG. 2B). The overall accuracy of the top two most possible organ systems was 66.8% (FIG. 8).

Example 4: Optimized Multi-Cancer Early Detection (MCED) Models Quantification of PTMs with Serum Peripheral blood was collected using a serum collection tube (such as BD Biosciences, San Jose, USA). Serum was separated within 4~6 hours using a centrifuge at 1300×g for 10 minutes at 4° C. A total of 500 μL of serum from each blood sample was used to measure the levels of ten designated PTMs, including AFP, CA125, CA15-3, CA19-9, CA72-4, CEA, CYFRA 21-1, ProGRP, SCC, and PSA, by using electrochemiluminescence immunoassay (such as Roche cobas e411/e601 or Bioplex 200 platform) and commercially available reagent kits following manufacturer's instructions.

Quantification of PTMs with Plasma

Peripheral blood was collected using a Cell-Free DNA BCT (such as Streck, La Vista, USA). When using Streck blood collection tube, the blood sample could be kept at room temperature and conducted plasma separation within 3~5 days. Plasma samples were separated by centrifugation at 1600×g for 10 minutes at 4 C, followed by further centrifugation of the supernatant at 16,000×g for 10 minutes at 4° C. A total of 500 μL of plasma from each blood sample was used to measure the levels of ten designated PTMs, including AFP, CA125, CA15-3, CA19-9, CA72-4, CEA, CYFRA 21-1, ProGRP, SCC, and PSA, by using electrochemiluminescence immunoassay (such as Roche cobas e411/e601 or Bioplex 200 platform) and commercially available reagent kits following manufacturer's instructions.

Optimization of Multi-Cancer Early Detection (MCED) Models

Figure 9:
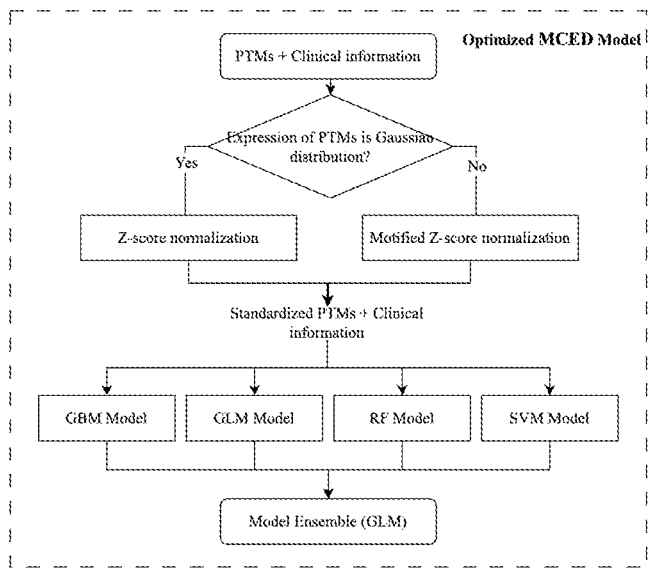
FIG. 9 shows the process of the optimized multi-cancer early detection (MCED) model.

We developed a blood-based and cost-efficient MCED test, which utilized a panel of selected protein tumor markers expression and the clinical information (such as: age and gender) to build an artificial intelligence (AI) model to distinguish cancer patients from non-cancer individuals by calculating the probability of cancer (POC) index (FIG. 9). We have a large study (n=9382) containing more than nine common cancer types (breast, colorectum, liver, lung, lymphoma, oesophagus, ovary, pancreas, and stomach) from three independent source and dominated by early-stage patients (63.2% stage I and II). Samples were divided into training (n=1646, the samples were from SeekIn Inc, Shenzhen, China) and independent validation cohort 1 (n=5919, the samples were from a partner hospital), and independent validation cohort 2 (n=1817, the samples were from Johns Hopkins University School of Medicine published study).

We utilized the training cohort consisting of 1646 samples, each with the expression levels of 7 selected protein tumor markers (AFP, CA125, CA15-3, CA19-9, CA72-4, CEA, CYFRA 21-1) as well as clinical information such as age and gender. Firstly, we used Z-score method to do the normalization, which was a common method used to normalize data by transforming it to have a mean of 0 and a standard deviation of 1. However, if the expression of any protein marker was not a Gaussian distribution, such as having skewness or containing outliers, Modified Z-Score could better handle these non-normal distributed data as it calculated the difference between the observation and the median divided by the median absolute deviation (MAD).

After normalization, these data set were used to develop an MCED (Multi-Cancer Early Detection) model through AI method, such as Gradient Boosting Machine (GBM), Generalized Linear Model (GLM), Random Forest (RF), and Support Vector Machine (SVM). These AI methods were employed to build different models capable of distinguishing between cancer and non-cancer individuals.

To optimize the model performance, a 10-fold cross-validation was performed for each AI methods. The cross-validation process generated average cancer predicting scores from each AI method, ranging from 0 to 1. These average cancer predicting scores from all four AI methods were combined into a matrix, which served as input for a second layer GLM algorithm. The GLM algorithm integrated these scores from different AI method and built a final ensemble model to generate the final probability of cancer, referred to as the Probability of Cancer (POC) index, for each test sample. Higher POC index indicated a higher probability of the test sample with cancer. The performance of the MCED model and its robustness were validated using two independent cohorts.

This comprehensive approach aimed to combine models trained using different methods. The model ensemble can capture different aspects of the data and reduce the risk of overfitting, and enhance the accuracy and reliability of the MCED model for cancer detection. Compared with EXAMPLE 1, an additional 18 cancer patients could be detected by the optimized MCED model. The sensitivity was 61.3% at the same specificity 90.0%, showing 3.1% sensitivity increase.

Example 5: Combining the Optimized MCED Model with the Outlier Analysis

Due to that MCED model was a multi-cancer early screening model, certain protein biomarkers related to multiple cancer types had a greater contribution or higher weights in the model. Conversely, certain biomarkers that were highly specific to a particular cancer type (e.g., AFP specifically for liver cancer detection) had relatively lower contributions. This led to cases where a highly specific protein biomarker for a certain cancer type exhibited abnormally high level (while others protein markers remained normal), and the MCED model could predict a lower Probability of Cancer (POC) index.

Figure 10:
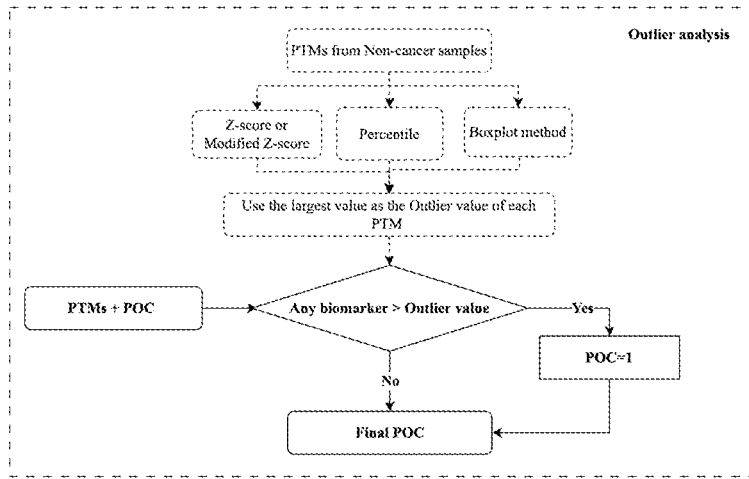
FIG. 10 shows the process of Outlier analysis.

To address this issue, an Outlier Analysis approach was developed to predict these types of cancer patients (FIG. 10). The Outlier Analysis method focused on identifying and analyzing cases where a highly specific cancer biomarker showed exceptional expression levels compared to normal cases. By incorporating this approach into the MCED model, the detection of cancer patients who may have exhibited unique biomarker expressions was improved, providing more accurate predictions and insights for multi-cancer early cancer diagnosis. Here, we used the three methods below to determine the cutoff value for outlier analysis, based on more than 6000 non-cancer samples.

1) Box plot method: The box plot method is used to identify outliers by plotting the protein tumor marker expression from normal control samples. A box plot displays the quartile range of the data, and observations that exceed the upper quartile plus 1.5 times the inter-quartile range can be considered as outliers' cutoff value.

2) Modified Z-Score: Since some non-cancer diseases can also result in elevated protein tumor markers expression levels in normal control cohort, the protein expression levels in the normal control cohort exhibit skewness (FIG. 11). Therefore, the modified Z-score is considered the data skewness by calculating the difference between the observation and the median divided by the median absolute deviation (MAD). The expression of protein tumor markers with modified Z-score>10 is defined as outliers' cutoff value.

3) Percentile: The percentile method compares the observation with the percentiles of the data, and observations that exceed the 99th percentile of the normal cohort can be considered as outliers' cutoff value.

Based on the cutoff values obtained from the above three methods, the maximum value is selected as the final abnormal high outliers' cutoff value. If the expression level of a particular biomarker in a test sample is greater than the corresponding abnormal cutoff value, the sample can be predicted as cancer patient. Through the development of this outlier analysis method, we aim to enhance the identification of cancer patients with significantly abnormal level of one cancer specific protein biomarker. By effectively predicting these exceptional cases, we can provide valuable insights into the potential presence of specific types of cancer and aid in early detection.

Figure 12:
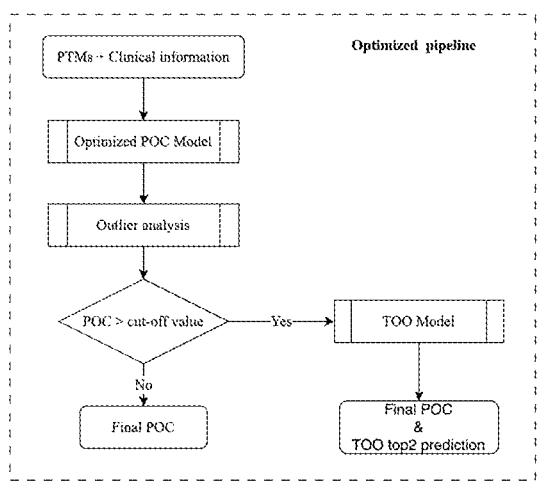
FIG. 12 shows the process of optimized pipeline.
Figure 13:
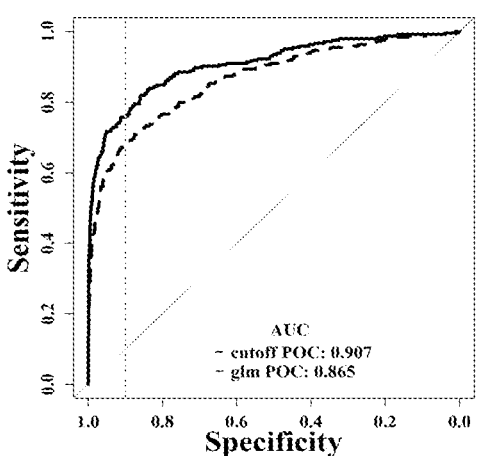
FIG. 13 shows the receiver operating characteristic (ROC) curves using an Outlier Analysis approach for liver detection.

For example, as AFP is a specific biomarker for liver cancer, its importance is relatively low in our multi-cancer early detection model. However, by incorporating the above outlier analysis, we can improve the sensitivity of liver cancer detection. Through outlier analysis, AFP outlier cutoff value was 614.4 IU/ml. Based solely on the MCED model (FIG. 2A), 154 out of 244 liver cancer samples were successfully predicted as positive. The sensitivity was 63.1% (95% confidence interval: 56.7%, 69.2%) at the specificity of 92.9% (95% CI: 92.3%, 93.5%). By combining the outlier analysis with the optimized MCED model (FIG. 12), an additional 23 positive samples were successfully predicted, resulting in a total of 177 positive samples. The sensitivity increased to 72.5% (95% confidence interval: 66.5%, 78.0%), showing a 9.4% improvement, while the specificity had a slight increase with 93.4%. As show in FIG. 13, the AUC was increased to 0.907 from 0.865, and the Delong's test showed the AUC value had a significant increase (P<0.001).

Example 6: PTMs Analysis for the Post-Surgery Samples 32 hepatocellular carcinoma (HCC) patients who underwent radical surgery from May 2018 to February 2022 were recruited. The inclusion criteria were as follows: (a) HCC confirmed by pathology, (b) no preoperative anti-tumor treatment, and (c) R0 resection. The exclusion criterion was as follows: presence or history of malignancies in extrahepatic organs. All participants provided written informed consent upon enrollment. Peripheral blood (8 mL) after surgery were collected from each patient with Streck tubes (Streck, Omaha, USA).

Plasma separating from blood was utilized for quantifying the expression levels of 7 PTMs (AFP, CA125, CA15-3, CA19-9, CA72-4, CEA, CYFRA 21-1). The POC index was calculated as per EXAMPLE 5. For post-surgery samples, a minimal residual disease MRD+ status was defined if the POC index was greater than 0.9, while an MRD-status was assigned if POC<=0.9. Following surgery, 20 out of 32 patients were MRD−, exhibiting significantly improved Overall Survival (OS) compared to the remaining 12 MRD+ samples (log-rank test: p<0.05, FIG. 14A). Moreover, within the MRD-status HCC patients, there was no difference in OS between those who received treatment after surgery and those who did not (log-rank test: p=0.55, FIG. 14B). These findings underscore the effectiveness of our method in detecting MRD status for predicting the prognosis of early-stage HCC patients and distinguishing HCC patients with MRD-who may not require systemic treatment.

Example 7:10 PTMs for Cancer Screening 533 blood samples were collected from cancer patients (397) and individuals without cancer (156). After separation, plasma or serum was used to quantify the expression levels of PTMs using a common method. In this case, an electro-chemiluminescence immunoassay (Roche cobas e411/e601) was utilized along with corresponding commercially available assay kits compatible with this platform (e.g., Roche Elecsys SCC assay kit for detecting SCC levels). According to the manufacturer's instructions, the concentrations of 10 PTMs in these samples were quantified, including AFP, CA125, CA15-3, CA19-9, CA72-4, CEA, CYFRA 21-1, ProGRP, SCC, and PSA (or TPSA). Since PSA is prostate-specific antigen, it is not necessary for females. Each female sample only includes 9 protein tumor markers without PSA.

At least 7 PTMs selected from the 10 PTMs can be used for multi-cancer early detection (MECD) by a previous approach. In this case, expression levels of 9 PTMs (AFP, CA125, CA15-3, CA19-9, CEA, CYFRA 21-1, ProGRP, SCC, PSA) were selected from 533 blood samples. Similarly, for females, only 8 PTMs (excluding PSA and CA72-4) were selected. These PTMs for females are AFP, CA125, CA15-3, CA19-9, CEA, CYFRA 21-1, ProGRP, and SCC. Due to the limited sample size, model overfitting is possible with ensemble modeling. Therefore, the GLM algorithm was used to establish the model, followed by the method as described in EXAMPLE 5 to analyze outliers and determine outlier cutoff values for protein tumor markers, which further enhanced the model's sensitivity for multi-cancer early screening.

Figures 15A, 15B:
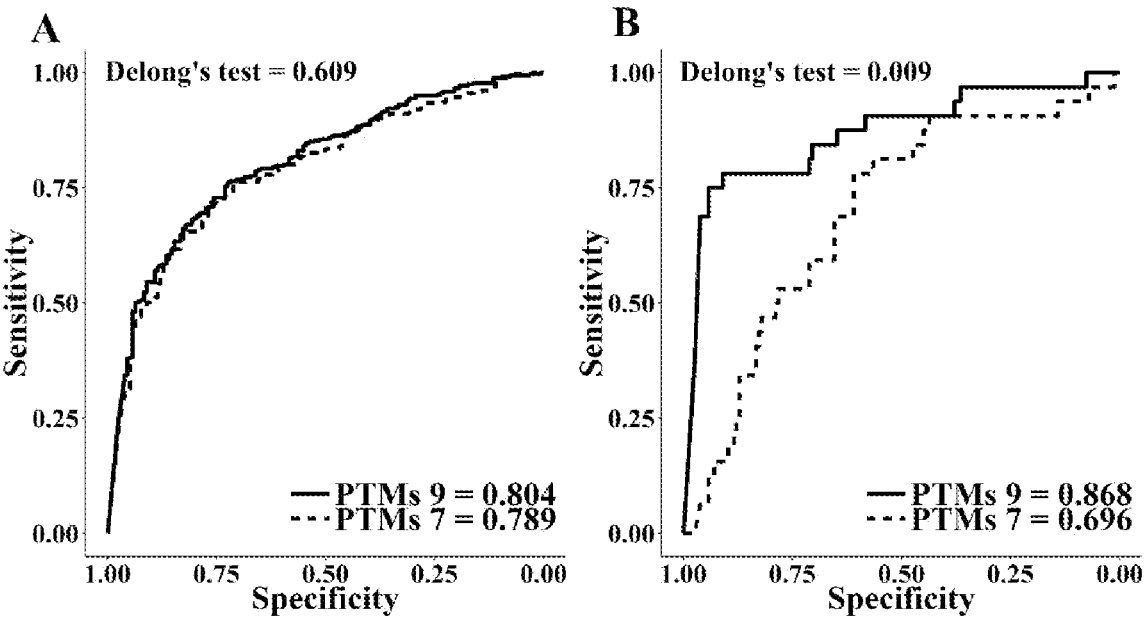
FIGS. 15A-15B illustrate a comparison of receiver operating characteristic (ROC) curves for different numbers of PTMs.

The model combining the 9 markers with the outlier method reached an AUC value of 0.811 for cancer detection in the samples, with a specificity of 90.4% (95% confidence interval: 84.6% to 94.5%) and sensitivity of 56.9% (95% confidence interval: 51.9% to 61.9%). As shown in FIGS. 15A-15B, using the same dataset, the model including the 9 PTMs showed no significant differences (DeLong's test: p-value=0.609) from the model including the 7 PTMs (EXAMPLE 5, AFP, CA125, CA15-3, CA19-9, CA72-4, CEA, CYFRA 21-1) in some cancer types, which included bile duct cancer, breast cancer, colorectal cancer, endometrial cancer, esophageal cancer, gallbladder cancer, liver cancer, lung cancer, ovary cancer, pancreas cancer, stomach cancer. It showed significant differences (DeLong's test: p-value=0.009) in new types of cancer (small cell lung cancer (SCLC), prostate cancer, cervical cancer). In total, the 9 PTMs could cover more cancer types and achieve adequate sensitivity, significantly improving the sensitivity of three common cancer types (lung cancer, prostate cancer, and cervical cancer).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for early detection of the presence of cancer in a subject, the method comprising:

(a) collecting a blood sample of the subject;

(b) quantifying the level of a panel of biomarkers from the blood sample of the subject using one or more immunoassays, wherein the panel of biomarkers comprises AFP, CA125, CA15-3, CA19-9, CEA, and CYFRA 21-1;

(c) training a machine learning system to generate a classifier using a plurality of parameters for inputs on a cohort population comprising a group of cancer patients and a group of non-cancer individuals using a machine learning algorithm selected from the group consisting of Generalized Linear Model (GLM), Gradient Boosting Machine (GBM), Random Forest (RF), and Support Vector Machine (SVM), wherein the plurality of parameters comprises the level of the panel of biomarkers and at least one clinical parameter;

(d) determining a cancer predicting score of the subject by applying the classifier obtained in step (c) to the quantified level of the panel of biomarkers obtained in step (b) together with the at least one clinical parameter of the subject;

(e) performing an Outlier Analysis by:

(i) determining a cut-off value for each biomarker in the panel of biomarkers in step (b), wherein the cut-off value for a biomarker represents an abnormal high level of the biomarker in non-cancer individuals, (ii) comparing the quantified level of each biomarker in step (b) with the corresponding cut-off value, wherein:

if any of the quantified level of the panel of biomarkers in step (b) is higher than the corresponding cut-off value, assigning a cancer predicting score to the subject that indicates the subject has cancer; and if none of the quantified level of the panel of biomarkers in step (b) is higher than the corresponding cut-off value, assigning the cancer predicting score obtained in step (d) to the subject, wherein the cancer predicting score obtained in step (d) is an indicator of whether the subject has cancer (f) determining that the subject has cancer; and (g) treating the subject with a cancer therapy, wherein the subject has lung cancer, breast cancer, colorectal cancer, stomach cancer, liver cancer, cervical cancer, esophageal cancer, pancreatic cancer, ovarian cancer, or lymphoma; wherein the cancer therapy comprises surgery or chemotherapy.

2. The method of claim 1, wherein the plurality of parameters further comprises X-ray imaging, mammography, computerized tomography (CT), or Magnetic Resonance Imaging (MRI).

3. The method of claim 1, wherein the panel of biomarkers are selected from at least seven different biomarkers selected from AFP, CA125, CA15-3, CA19-9, CEA, CYFRA 21-1, ProGRP, SCC, and PSA.

4. The method of claim 1, wherein the panel of biomarkers comprises or consists of AFP, CA125, CA15-3, CA19-9, CA72-4, CEA, and CYFRA 21-1.

5. The method of claim 1, wherein the subject is a male and the panel of biomarkers comprises or consists of AFP, CA125, CA15-3, CA19-9, CEA, CYFRA 21-1, ProGRP, SCC, and PSA; or wherein the subject is a female and the panel of biomarkers comprises or consists of AFP, CA125, CA15-3, CA19-9, CEA, CYFRA 21-1, ProGRP, and SCC.

6. The method of claim 1, wherein the machine learning system is trained using GLM.

7. The method of claim 1, wherein the method comprises training the machine learning system using at least two machine learning algorithms selected from the group consisting of GLM, GBM, RF, and SVM.

8. The method of claim 7, wherein the method comprises applying GLM to the results from the at least two machine learning algorithms.

9. The method of any one of claim 1, wherein the quantified level of the panel of biomarkers is normalized by Modified Z-Score, wherein the Modified Z-Score is obtained by calculating the difference between the observed value and the median value, divided by the median absolute deviation (MAD).

10. The method of claim 1, wherein the method can aid early detection of the presence of at least two cancer types simultaneously.

11. The method of claim 1, wherein the panel of biomarkers consists of AFP, CA125, CA15-3, CA19-9, CEA, and CYFRA 21-1.

12. The method of claim 1, wherein the subject is a male and the panel of biomarkers comprises or consists of AFP, CA125, CA15-3, CA19-9, CEA, CYFRA 21-1, and PSA; or wherein the subject is a female and the panel of biomarkers comprises or consists of AFP, CA125, CA15-3, CA19-9, CEA, and CYFRA 21-1.

13. The method of claim 1, wherein the subject is a male and the panel of biomarkers comprises or consists of AFP, CA125, CA15-3, CA19-9, CEA, CYFRA 21-1, SCC, and PSA; or wherein the subject is a female and the panel of biomarkers comprises or consists of AFP, CA125, CA15-3, CA19-9, CEA, CYFRA 21-1, and SCC.

14. The method of claim 1, wherein the method further comprises determining the tissue of origin (TOO) in the subject, wherein the subject is indicated to have a cancer based on the machine learning-based supervised algorithm using the panel of biomarkers.

15. The method of claim 1, wherein the one or more immunoassays are conducted using an automated immunoassay analyzer.

16. The method of claim 1, wherein the one or more immunoassays comprise an enzyme-linked immunosorbent assay (ELISA), a chemiluminescent immunoassay (CLIA), a fluoroimmunoassay (HA), an electrochemiluminescence immunoassay, an enzyme immunoassay (EIA), a radioimmunoassay (RIA), a counting immunoassay (CIA), a filter media enzyme immunoassay (META), a fluorescence-linked immunosorbent assay (FLISA), an agglutination immunoassay, a multiplex fluorescent immunoassay, or an immunohistochemistry assay.

17. The method of claim 1, wherein the machine learning system is trained on at least 1000 subjects.

* * * * *